(12) United States Patent
Buehler et al.

(10) Patent No.: US 8,876,859 B2
(45) Date of Patent: Nov. 4, 2014

(54) DEVICES FOR PERFORMING BLEPHAROPLASTY AND METHODS OF USING THE SAME

(76) Inventors: Patricia Buehler, Bend, OR (US); Matthew W. Hoskins, Bend, OR (US)

( * ) Notice: Subject to any disclaimer, the term of this patent is extended or adjusted under 35 U.S.C. 154(b) by 183 days.

(21) Appl. No.: 13/324,920

(22) Filed: Dec. 13, 2011

(65) Prior Publication Data

US 2012/0149990 A1    Jun. 14, 2012

Related U.S. Application Data

(60) Provisional application No. 61/422,915, filed on Dec. 14, 2010.

(51) Int. Cl.
| | | |
|---|---|---|
| *A61B 1/32* | (2006.01) | |
| *A61B 17/02* | (2006.01) | |
| *A61B 17/28* | (2006.01) | |
| *A61B 17/122* | (2006.01) | |
| *A61B 17/04* | (2006.01) | |
| *A61B 17/072* | (2006.01) | |
| *A61B 18/00* | (2006.01) | |
| *A61B 19/00* | (2006.01) | |
| *A61B 17/32* | (2006.01) | |
| *A61B 18/14* | (2006.01) | |
| *A61B 17/00* | (2006.01) | |

(52) U.S. Cl.
CPC .......... *A61B 17/122* (2013.01); *A61B 17/2833* (2013.01); *A61B 2017/1225* (2013.01); *A61B 17/0482* (2013.01); *A61B 2017/07285* (2013.01); *A61B 2018/00601* (2013.01); *A61B 17/1227* (2013.01); *A61B 17/0206* (2013.01); *A61B 2018/00589* (2013.01); *A61B 17/072* (2013.01); *A61B 2019/465* (2013.01); *A61B 2017/2808* (2013.01); *A61B 17/28* (2013.01); *A61B 2017/320052* (2013.01); *A61B 18/1442* (2013.01); *A61B 2017/07221* (2013.01); *A61B 2017/00792* (2013.01)
USPC ........................................................ 606/210

(58) Field of Classification Search
USPC ......... 600/208, 210, 215, 217, 218, 221, 235, 600/236; 606/88, 105
See application file for complete search history.

(56) References Cited

U.S. PATENT DOCUMENTS

| | | | | |
|---|---|---|---|---|
| 1,401,190 | A | * | 12/1921 | Risley ............................ 600/215 |
| 2,679,249 | A | | 5/1954 | Weihmann |
| 3,054,398 | A | * | 9/1962 | Kobler .......................... 600/206 |
| 4,321,916 | A | * | 3/1982 | McKee ......................... 600/209 |
| 4,542,742 | A | | 9/1985 | Winkelman et al. |

(Continued)

OTHER PUBLICATIONS

Angres, "A simple approach to blepharoplasty using the Angres II blepharopigmentation lid clamp," *Ann Ophthalmol.* 20(9):349-51, 1988.

(Continued)

*Primary Examiner* — Andrew Yang
*Assistant Examiner* — Diana S Jones
(74) *Attorney, Agent, or Firm* — Klarquist Sparkman, LLP

(57) ABSTRACT

A blepharoplasty device includes a handle member, an elongate, curved first jaw member coupled to the handle member and having a first tissue contacting surface, and an elongate, curved second jaw member coupled to the handle member and having a second tissue contacting surface. The first and second jaw members are moveable relative to one another between a closed position and an open position to capture eyelid tissue and facilitate the cutting and subsequent reattachment of the eyelid tissue.

17 Claims, 15 Drawing Sheets

(56) References Cited

U.S. PATENT DOCUMENTS

| | | |
|---|---|---|
| 4,557,265 A | 12/1985 | Anderson |
| 4,917,677 A | 4/1990 | McCarthy |
| 5,070,860 A * | 12/1991 | Grounauer .................... 600/236 |
| 5,534,008 A | 7/1996 | Acksel |
| 5,728,112 A | 3/1998 | Yoon |
| 5,984,934 A | 11/1999 | Ashby et al. |
| 6,283,913 B1 | 9/2001 | Seibel |
| 6,346,078 B1 | 2/2002 | Ellman et al. |
| 7,146,895 B2 | 12/2006 | Kong et al. |
| 7,252,667 B2 | 8/2007 | Moses et al. |
| 7,384,421 B2 | 6/2008 | Hushka |
| 2007/0244516 A1 | 10/2007 | Chin et al. |

OTHER PUBLICATIONS

Fredriksson et al., "New mechanical device for effective removal of skin tags in routine health care," *Dermatology Online Journal* 15(2):9, 2009.

Keyhani et al., "Modified technique and ptosis clamp for surgical correction of congenital pediatric ptosis by anterior levator resection," *Facial Plast Surg.* 23(3):156-61, 2007.

Seltzer, "A new fenestrated instrument for blepharoplasty for upper eyelid," *J Natl Med Assoc.* 68(3):217-218, 1976.

Small et al., "A New Upper Blepharoplasty Clamp," *Ophthalmic Plast Reconst Surg.* 1:103-105, 1985.

* cited by examiner

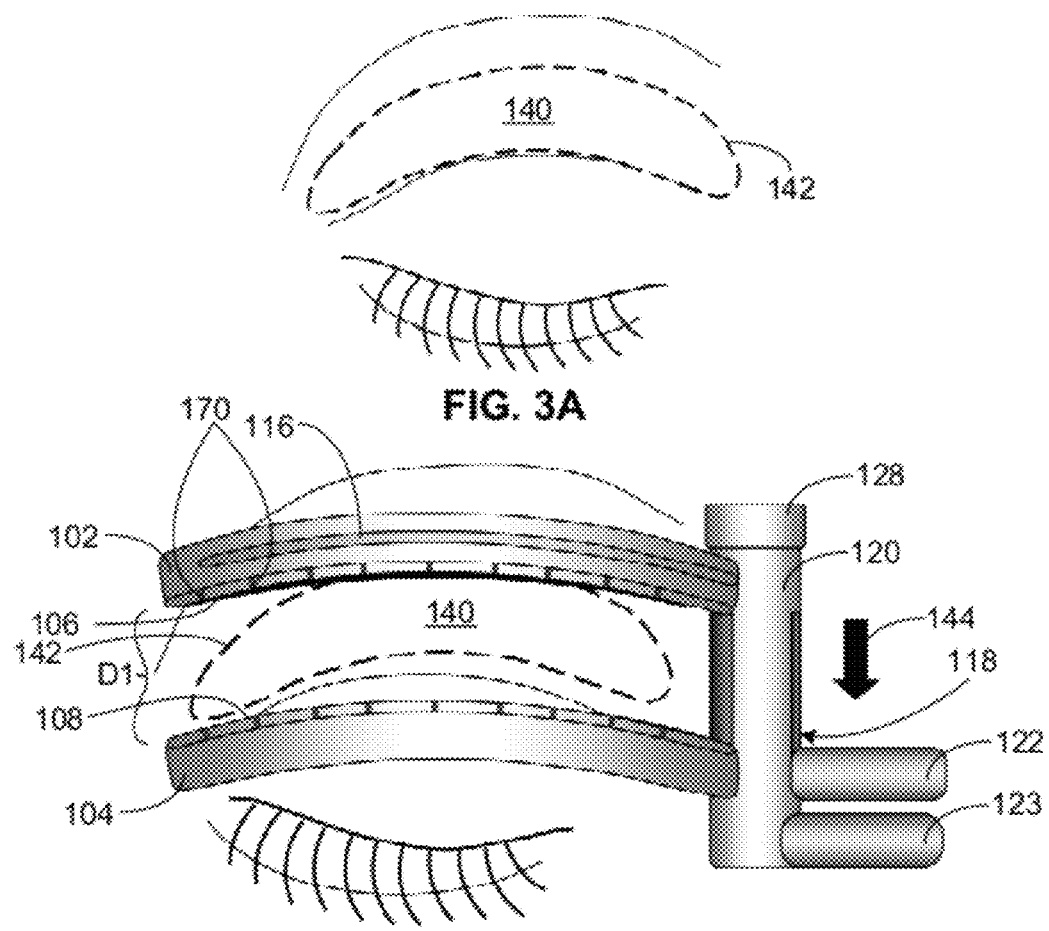
FIG. 3A
FIG. 3B
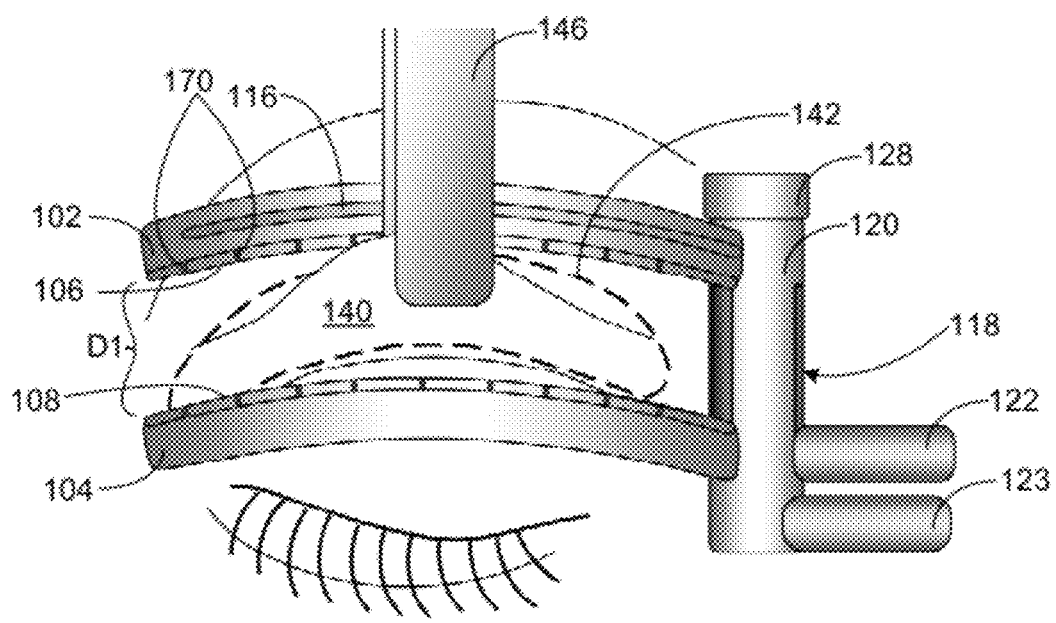
FIG. 3C

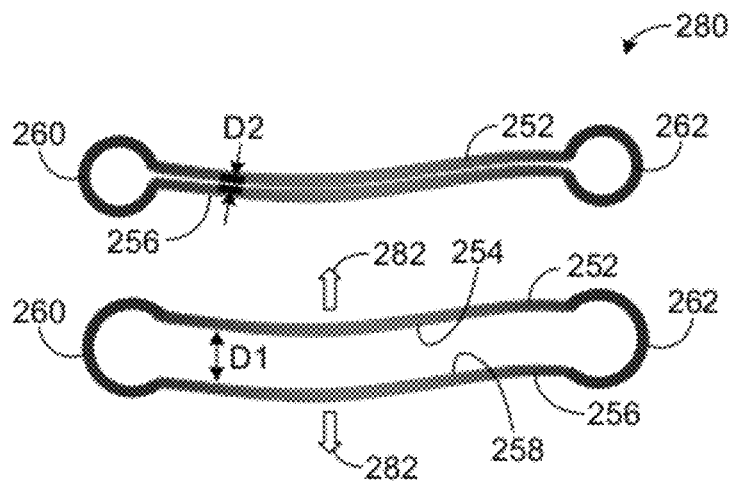
FIG. 15A
FIG. 15B
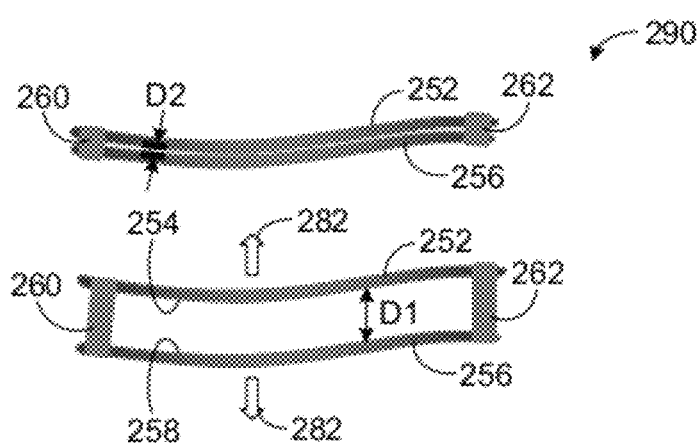
FIG. 16A
FIG. 16B
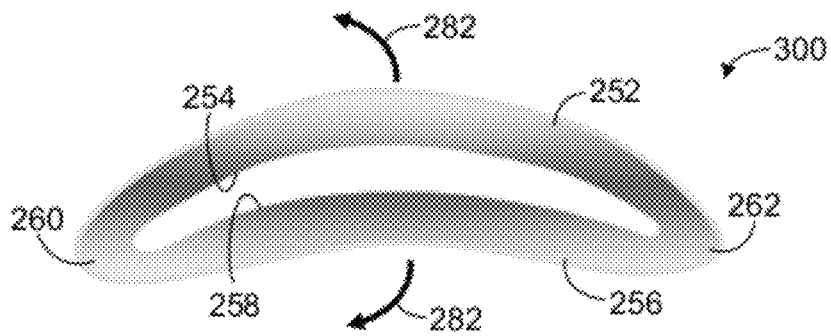
FIG. 17

DEVICES FOR PERFORMING BLEPHAROPLASTY AND METHODS OF USING THE SAME

CROSS REFERENCE TO RELATED APPLICATION

This application claims the benefit of priority of U.S. Provisional Application No. 61/422,915, filed Dec. 14, 2010, which is herein incorporated by reference in its entirety.

FIELD

The present disclosure relates to devices for performing blepharoplasty and methods for using the same.

BACKGROUND

Blepharoplasty is a surgical procedure that removes excess skin and/or fat from the eyelids of a patient. The surgery is most commonly performed on patients who are middle-aged or older for aesthetic reasons to reduce bagginess and wrinkles. However, the surgery can also be performed for functional reasons, such as to improve the vision of individuals whose upper eyelids have sagged into their field of vision. To address upper eyelid laxity, the surgeon can remove a segment of skin in the upper eyelid and then attach the edges of the resulting cut tissue together to tighten the appearance of skin above the eye. In some cases, prior to closing the incision, the surgeon will also remove excess muscle and fat sitting beneath the eyelid. The surgery is generally performed under local anesthesia or light sedation, and typically takes between about one and three hours.

Good cosmetic and functional results are dependent on the location of the incision and removal of the proper amount of tissue. Symmetry is also desirable to achieve a pleasing result, hence the surgeon generally attempts to provide a similar amount of eyelid lift and smoothing on both eyes.

Conventional blepharoplasty procedures suffer from several deficiencies. For example, to achieve the desired symmetry, multiple cutting steps may be required to ensure that the appropriate amount of tissue is removed from one or both eyelids. Surgical time may also be required to compare skin removed from one eyelid to skin removed from another eyelid to determine whether the amount of skin removed from both eyelids is substantially the same. Such efforts can undesirably increase the length of the procedure. Additionally, even if significant care is taken, conventional blepharoplasty procedures can result in a lack of symmetry or uniformity between the eyes of the patient.

SUMMARY

In a first embodiment, a blepharoplasty device includes a handle member, an elongate, curved first jaw member coupled to the handle member and having a first tissue contacting surface, and an elongate, curved second jaw member coupled to the handle member and having a second tissue contacting surface. The first and second jaw members are moveable relative to one another between a closed position and an open position. The first and second tissue contacting surfaces can be spaced apart a distance D1 in the open position and a distance D2 in the closed position. A biasing member can be provided to bias the device towards the closed position, and an actuator can be provided to counter the biasing member and move the device into the open position. The distance D2 is smaller than the distance D1, with the distance D1 being sized to allow the insertion of eyelid tissue between the first and second tissue contacting surfaces and the distance D2 being sized to capture and secure the eyelid tissue inserted between the first and second tissue contacting surfaces.

In some embodiments, the first jaw member is fixedly coupled to the handle member and the second jaw member is movable relative to the handle member to allow relative movement of the first and second jaw members. The actuator can include an arm member that is fixedly coupled to the second jaw member and movement of the arm member relative to the handle causes the device to move between the closed and open positions. The biasing member can include a spring member that is coupled to the arm member, with the spring member exerting a force on the arm member to bias the second jaw member towards the first jaw member.

In some embodiments, the first and second jaw members can extend from the handle member in a generally cantilevered manner and the handle member can have a main body that extends generally perpendicularly to the first and second jaw members. The arm member can extend perpendicularly from the main body of the housing member.

In some embodiments, a pressure adjustment member is provided. The pressure adjustment member can be moveable between a first position and a second position to adjust the distance D2 and vary a pressure exerted on the first and second tissue contacting surfaces in the closed position. The pressure adjustment member can be moveable to decrease the distance D2 and increase the pressure on eyelid tissue captured between the first and second tissue contacting surfaces. In some embodiments, the pressure adjustment member includes a set screw.

In some embodiments, a cutting guide is formed in one or both of the first and second jaw members. The cutting guide can be configured to receive a portion of a cutting tool to guide the cutting tool across the length of first and second jaw members. In other embodiments, a cutting tool can be received in the cutting guide provided in the device. The cutting tool can be moveable across a length of the first and second jaw members of the device to cut a portion of the eyelid tissue in a predetermined path defined by the cutting guide. Alternatively, the cutting tool can be vertically movable between the first and second jaw members to cut a portion of the eyelid tissue in a predetermined path defined by the cutting guide. The cutting tool can include an electrode cutting blade that is configured to operate at a first cutting frequency and a second cauterizing frequency.

In some embodiments, the device includes a plurality of suture guides formed in the first and second jaw members. A continuous suturing mechanism can also be provided, with the continuous suturing mechanism including a rotatable member configured to direct a suture needle through the plurality of suture guides. In other embodiments, a stapling device can be coupled to the first and second jaw members to deliver staples to attach portions of the eyelid tissue in the closed position. In other embodiments, a plurality of retraction members can be coupled to the first and second jaw members. The retraction members can be configured to grip portions of the eyelid tissue while the device is in the closed position such that movement of the device to the open position causes adjacent edges of the eyelid tissue to separate. In other embodiments, the first and second tissue contacting surfaces include cushion members that extend from inner surfaces of the first and second jaw members.

In another embodiment, a method of performing a blepharoplasty procedure includes providing a blepharoplasty device with an elongate, curved first jaw member and an elongate, curved second jaw member. The first and second jaw members can be biased towards a closed position by a biasing force. The first and second jaw members can be moved into an open position by exerting a force on the first and second jaw members to counter the biasing force of the device. Eyelid tissue can be positioned between tissue contacting surfaces of the first and second jaw members. The first and second jaw members can be moved into the closed position to capture the eyelid tissue between the first and second jaw members by reducing the force exerted on the first and second jaw members. The pressure on the eyelid tissue captured between the first and second jaw members can be increased by adjusting the distance between the first and second jaw members in the closed position.

In some embodiments, the pressure on the eyelid tissue is increased by rotating an adjusting member. The rotation of the adjusting member decreases the distance between the first and second jaw members in the closed position. In other embodiments, the method includes cutting the eyelid tissue by moving an integrated cutting tool through a cutting guide and across a portion of the eyelid tissue. In other embodiments, the method includes suturing the cut portion of the eyelid tissue together by directing a suture needle through a plurality of suture guides formed in the first and second jaw members.

In other embodiments, the method includes retracting the cut portion of the eyelid tissue by gripping the cut tissue with retraction hooks coupled to the first and second jaw members and moving the first and second jaw members to the open position, excising tissue underneath the cut portion of the eyelid tissue, and moving the first and second jaw members to the closed position.

In another embodiment, a blepharoplasty device includes first and second curved jaw members. The first curved jaw member has a first end and a second end, and the second curved jaw member has a first end and a second end. The first end of the first jaw member is coupled to the first end of the second jaw member and the second end of the first jaw member is coupled to the second end of the second jaw member. The first and second jaw members are moveable between a closed position and an open position in which the first and second jaw members are spaced apart a distance D1. The first and second jaw members are biased towards the closed position and are movable to the open position when an inwardly directed, compressive force is applied to the first and second ends of both of the first and second jaw members.

In another embodiment, a method of performing a blepharoplasty procedure includes providing a blepharoplasty device with a first jaw member having a first end and a second end, and a second jaw member having a first end and a second end. The first end of the first jaw member is coupled to the first end of the second jaw member and the second end of the first jaw member is coupled to the second end of the second jaw member. The method includes applying a compressive force to both the first and second ends of the first and second jaw members to cause tissue contacting surfaces of the first and second jaw members to move apart from one another. The tissue contacting surfaces are between the first and second ends of the first and second jaw members. The method includes positioning eyelid tissue between the tissue contacting surfaces of the first and second jaw members, and reducing the compressive force exerted on the first and second ends of the first and second jaw members to move the first and second jaw members into a closed position to capture the eyelid tissue between the tissue contacting surfaces of the first and second jaw members. Blood flow to the skin captured between the first and second jaw members is reduced or occluded by a biasing force exerted on the eyelid tissue by the device. In some embodiments, the tissue between the clamps eventually sloughs off without an incision being made and the edges of the remaining tissue between the clamps fuses together without suturing.

The foregoing and other objects, features, and advantages of the invention will become more apparent from the following detailed description, which proceeds with reference to the accompanying figures.

BRIEF DESCRIPTION OF THE DRAWINGS

FIG. 3A illustrates an outline of an area of an eyelid that is marked for removal.

FIG. 3B illustrates a device for performing a blepharoplasty procedure, with the device shown in an open position prior to moving tissue between clamping surfaces of the device.

FIG. 3C illustrates the device of FIG. 3B, with the device shown in an open position with tissue moved between clamping surfaces of the device.

FIG. 15A illustrates another blepharoplasty device that comprises a pair of upper and lower elongate members coupled together, shown in a closed position.

FIG. 15B illustrates the blepharoplasty device of FIG. 15A, shown in an open position.

FIG. 16A illustrates another blepharoplasty device that comprises a pair of upper and lower elongate members coupled together, shown in a closed position.

FIG. 16B illustrates the blepharoplasty device of FIG. 16A, shown in an open position.

FIG. 17 illustrates another blepharoplasty device that comprises a pair of upper and lower elongate members coupled together, shown in an open position.

DETAILED DESCRIPTION

Various embodiments of blepharoplasty devices and their methods of use are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language. As used herein, the term "superior" means toward the top of the head of a patient and "inferior" means toward the feet of a patient.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

The devices and methods disclosed herein can generally improve the overall efficiency of a blepharoplasty procedure by simplifying the steps required to perform a blepharoplasty procedure, enhancing the consistency of the procedure, and/or promoting better healing of the patient after the procedure.

Various Methods and Systems for Surgical Removal of Excess Skin/Tissue

Figure 1A:
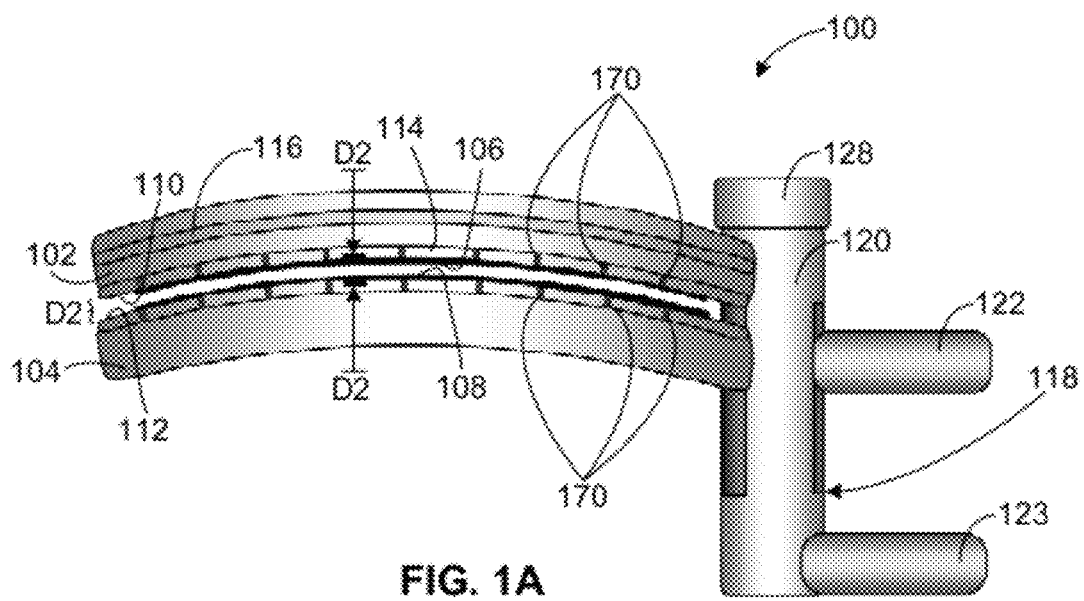
FIG. 1A illustrates a device for performing a blepharoplasty procedure, with the device shown in a closed position.
Figure 1B:
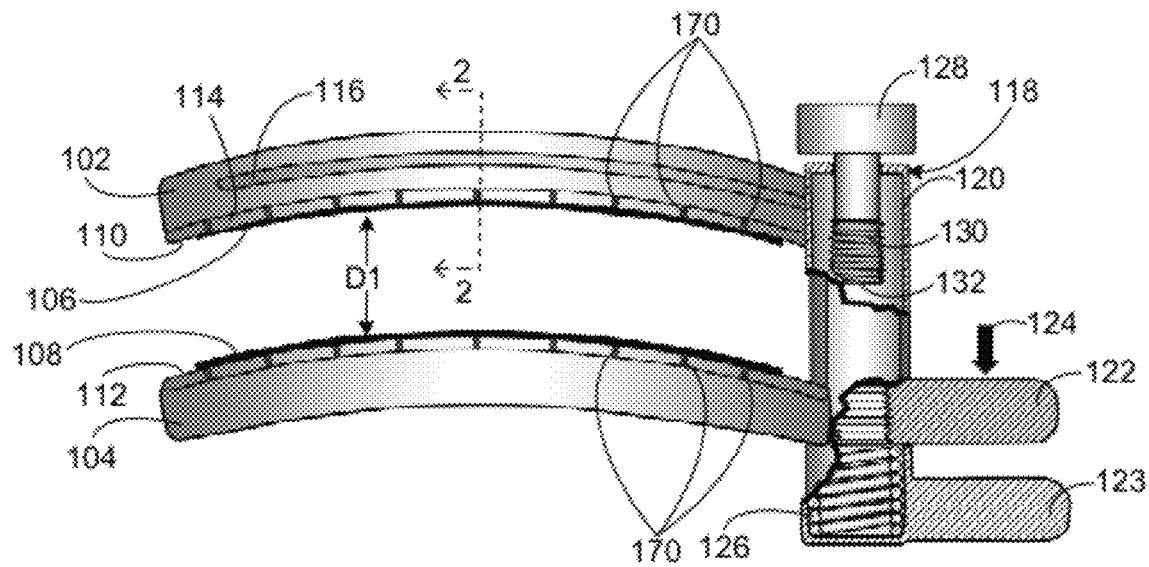
FIG. 1B illustrates a device for performing a blepharoplasty procedure, with the device shown in an open position.

FIGS. 1A and 1B illustrate an embodiment of a blepharoplasty device 100 that is configured to capture eyelid tissue to facilitate tissue excision from a portion of an eyelid. Device 100 is a tissue gripping device (e.g., a clamp) comprised of a pair of elongated jaw members 102, 104 operatively connected together so that they can be moved relative to one another between an open position (FIG. 1B) and a closed position (FIG. 1A). Upper jaw members 102 and lower jaw member 104 can be curved to follow a contour of the eyelid area to produce a desired incision shape.

In some embodiment, the radius of curvature of the upper and lower jaw members 102, 104 can be between about 0.5-1.0 inches. In addition, in some embodiments, the lengths of upper and lower jaw members 102, 104 can vary between about 1 and 2 inches.

In some embodiments, the upper and lower jaw member would be considered the superior jaw member and the lower jaw member would be considered the inferior jaw member because of their relative positions with respect to the head and feet. For purposes of simplicity, the terms "upper" and "lower" are used herein to refer to the superior and inferior members, although it should be understood that "upper" and "lower" do not imply any positional relationship aside from the anatomical reference points of the body.

Upper jaw member 102 has a first tissue contacting surface 106 and lower jaw member 104 has a second tissue contacting surface 108. First and second tissue contacting surfaces 106, 108 generally face one another in an opposing manner so that when eyelid tissue is positioned between upper and lower jaw members 102, 104, first and second tissue contacting surfaces 106, 108 can move towards one another to capture and secure the eyelid tissue between the first and second tissue contacting surfaces 106, 108.

When upper jaw member 102 and lower jaw member 104 are in the open position (FIG. 1B), first and second tissue contacting surfaces 106, 108 are separated by a distance D1 to form an opening or space that is large enough to receive eyelid tissue. As upper and lower jaw members 102, 104 move together to the closed position (FIG. 1A), the distance between first and second contacting surfaces 106, 108 is reduced to a distance D2. Distance D2 is selected so that the opening or space between first and second tissue contacting surfaces 106, 108 is small enough to capture and secure any eyelid tissue positioned between first and second tissue contacting surfaces 106, 108.

First and second tissue contacting surfaces 106, 108 are configured to grip and hold eyelid tissue that is positioned between the opposing first and second tissue contacting surfaces 106, 108. In some embodiments, first and second tissue contacting surfaces 106, 108 can comprise a cushion member that extends inwardly towards the captured tissue from an inner surface 110, 112 of upper and lower jaw members 102, 104, respectively, to reduce trauma to the captured tissue while it is gripped between first and second tissue contacting surfaces 106, 108. If a cushion member is not provided, the first and second tissue contacting surfaces 106, 108 can simply be the inner surfaces 110, 112 of upper and lower jaw members 102, 104.

Figure 2:
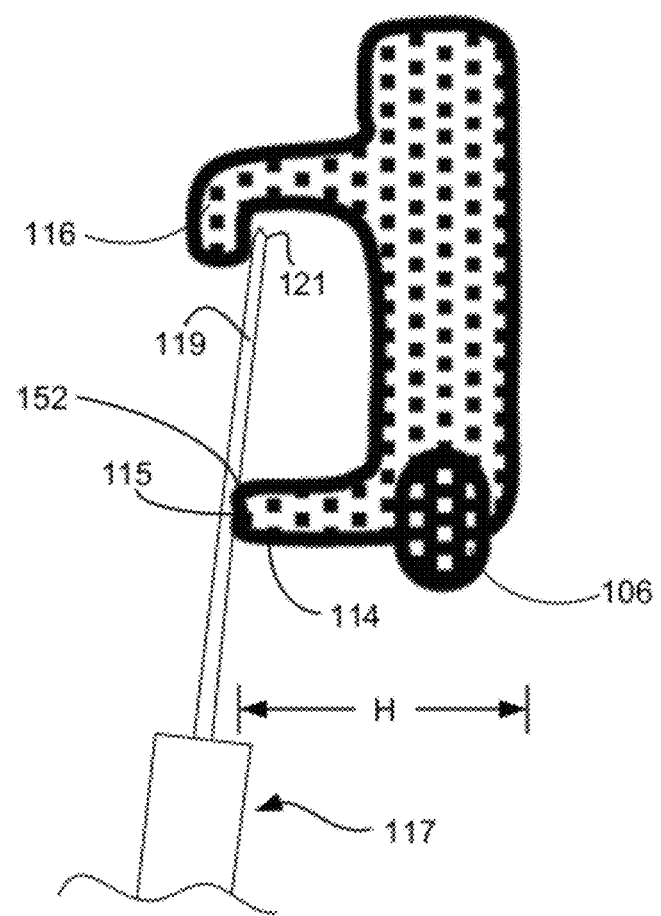
FIG. 2 illustrates a cross-section view of a portion of the device shown in FIG. 1B, with the cross-sectional view being taken along line 2-2 in FIG. 1B.

FIG. 2 illustrates a cross-sectional view of upper jaw member 102 taken along line 2-2 of FIG. 1B. As shown in FIG. 2, first tissue contacting surface 106 comprises a cushion member that extends inward (i.e., downward toward the area between upper and lower jaw members 102, 104) from the inner surface 110 of upper jaw member 102. Although FIG. 2 only illustrates a cross-sectional view of upper jaw member 102, it should be understood that lower jaw member 104 can have a similar structure; however, it should be understood that the structure of lower jaw member 104 will generally be a mirror image (i.e., have an inverted orientation) of the structure of upper jaw member 102. Thus, second tissue contacting surface 108 can comprise a cushion member that extends inward (i.e., upward toward the area between upper and lower jaw members 102, 104) from the inner surface 112 of lower jaw member 104.

Each of upper and lower jaw members 102, 104 can comprise one or more extension members that extend away from the patient to facilitate cutting of the tissue that is gripped between first and second tissue contacting surfaces. For example, as shown in FIG. 2, a first extension member 114 can extend from upper jaw member 102 in a direction away from the patient. In the embodiment shown in FIG. 2, the lower surface of first extension member 114 is co-extensive with the inner surface 110 of upper jaw member 102. The front surface 115 of first extension member 114 can serve as a guide for cutting the eyelid tissue by providing a surface over which the cutting edge of a cutting member (e.g., a blade) can move.

If desired, additional extension members can be provided on upper and lower jaw members 102, 104 to further guide the movement of a cutting member. For example, as shown in FIG. 2, a second extension member 116 can be provided superior to (i.e., in a direction away from first tissue contacting surface 106) first extension member 114. In some embodiments, second extension member can be curved or hooked to receive a top portion of a cutting member to facilitate and guide the cutting member as it moves across front surface 115 to cut the tissue of the eyelid. For example, FIG. 2 illustrates a cutting member 117 with a blade 119 that has a top portion 121 received in the curved portion of second extension member 116. As the blade 119 moves across front surface 115, the top portion 121 is received within the curved portion to help maintain a controlled movement of the blade 119 across the tissue captured between lower jaw member 104 and upper jaw member 102.

Device 100 can comprise an actuator 118 that is configured to move upper and lower jaw members between the open position (FIG. 1B) and the closed position (FIG. 1A) to capture eyelid tissue between first and second tissue contacting surfaces 106, 108 and/or to release any eyelid tissue captured therebetween. Actuator 118 can be operated by various mechanisms capable of causing relative movement between upper and lower jaw members 102, 104. The relative movement of upper and lower jaw members 102, 104 can be achieved by maintaining one jaw member in a fixed position relative to the other jaw member and moving the other jaw member towards or away from the fixed position jaw member. Alternatively, the relative movement of upper and lower jaw members 102, 104 can be achieved by moving both jaw members towards or away from one another, either concurrently or sequentially.

The embodiment shown in FIGS. 1A and 1B illustrates a device with one fixed jaw member and one moveable jaw member. In particular, upper jaw member 102 is shown coupled to handle member 120 in a fixed manner that restricts relative movement between upper jaw member 102 and handle member 120, and lower jaw member 104 is shown coupled to a movable first arm 122. First arm 122 is moveable relative to handle member 120 such that movement of first arm 122 causes respective movement of lower jaw member 104 relative to upper jaw member 102. Thus, by sliding first arm 122 downward (i.e., in the direction shown by arrow 124 in FIG. 1B), lower jaw member 104 also moves downward. As lower jaw member 104 moves downward, lower jaw member 104 moves away from upper jaw member 102 and the distance between first and second tissue contacting surfaces 106, 108 is increased. In some embodiments, a second arm 123 is provided to facilitate movement of first arm 122 relative to handle member 120. Thus, for example, upper and lower jaw members 102, 104 can be moved into the open position (FIG. 1B) by manually squeezing first and second arms 122, 123 together to exert a downward force on first arm 122.

First arm 122 and associated lower jaw member 104 can be biased towards the closed or open positions. For example, upper and lower jaw members 102, 104 can be spring-loaded or otherwise biased to automatically move into a closed or open position. Desirably, device 100 is biased closed to improve the ease with which tissue can be captured between the two jaw members 102, 104. FIGS. 1A and 1B illustrate an embodiment where lower jaw member 104 is biased towards the closed position (FIG. 1B) and upper and lower jaw members 102, 104 are configured to exert a pre-determined clamping force on tissue captured between first and second tissue contacting surfaces 106, 108 when device 100 moves into the closed position.

As shown in FIG. 1B, a spring member 126 can be provided to contact and exert a biasing force on first arm 122. The biasing force is directed upward (i.e., opposite the direction shown by arrow 124 in FIG. 1B) towards upper jaw member 102. Thus, in the absence of any other external force, upper and lower jaw members 102, 104 will move towards one another into the closed position. Spring member 126 is desirably selected so that the biasing force exerted by spring member 126 on lower jaw member 102 (via first arm 122) is strong enough to clamp and secure the eyelid tissue between first and second tissue contacting surfaces 106, 108. In addition the biasing force is also desirably strong enough to clamp the tissue in a manner that occludes blood flow into the tissue captured between first and second tissue contacting surfaces 106, 108. In this manner, the clamping force can reduce bleeding in the vicinity of the cut tissue after an incision is made.

As noted above, the closing of the gap between first and second tissue contacting surfaces 106, 108 reduces distance D1 to distance D2. When device 100 is in the closed position, the distance D2 between first and second tissue contacting surfaces 106, 108 can be substantially uniform across the length of upper and lower jaw members 102, 104. Because distance D2 is substantially uniform across the length of upper and lower jaw members 102, 104, the height of tissue caught between first and second tissue contacting surfaces 106, 108 will also be substantially uniform across the length of upper and lower jaw members 102, 104. Distance D2 can be small and, in some cases, can be zero. If the distance D2 is zero, first and second tissue contacting surfaces 106, 108 will contact each other if there is no tissue positioned between first and second tissue contacting surfaces 106, 108 in the closed position.

In some embodiments, distance D2 can be adjustable to conform to a particular characteristic of the patient undergoing the procedure, to conform to a surgeon's particular preferences, and/or to provide an intermediate gripping configuration that permits partial capture of tissue between first and second tissue contacting surfaces 106, 108. For example, an adjusting member 128 can be provided on handle member 120 to further adjust the distance between the two tissue contacting surfaces 106, 108.

As shown in FIG. 1B, adjusting member 128 can comprise a screw that has a threaded portion 130 and a bottom surface 132. The location of bottom surface 132 relative to handle member 120 can be adjusted by rotating adjusting member 128. The threaded portion 130 of the screw can be moved until it engages with a mating thread-receiving portion of lower jaw member 104. As threaded portion 130 engages with the mating thread-receiving portion of lower jaw member 104, lower jaw member 104 is drawn upward towards upper jaw member 102, increasing the amount of force exerted on the captured tissue. Thus, in operation, spring member 126 pushes lower jaw member 104 upwards until the tissue is captured between the upper and lower jaw members 102, 104. Then, the screw can be rotated to engage lower jaw member 104 and pull it toward upper jaw member 102 to achieve a finer adjustment the amount of force applied to the captured tissue.

In an alternative embodiment, rather than acting to move upper and lower jaw members 102, 104 together, the screw member can restrict movement of upper jaw member 102 relative to lower jaw member 104. For example, in this embodiment, as first arm 122 moves upward, an upper surface of an internal portion of arm 122 can be configured to contact bottom surface 132 so that first arm 122 is restricted from moving further upwards. By rotating adjusting member 128 in a first direction, threaded portion 130 can move further into handle member 120, thereby moving bottom surface 132 closer to first arm 122 and increasing the distance D2 between first and second tissue contacting surfaces 106, 108. By rotating adjusting member 128 in a second direction (opposite the first direction), threaded portion 130 can move out of handle member 120, thereby moving bottom surface 132 further from first arm 122 and decreasing the distance D2 between first and second tissue contacting surfaces 106, 108. As discussed in more detail below, the distance D2 can be adjusted via adjusting member 128 after tissue is captured between first and second tissue contacting surfaces 106, 108 to increase or decrease the pressure exerted on the tissue by first and second tissue contacting surfaces 106, 108.

Device 100 can also include a mechanism that locks or restricts relative movement of the upper and lower jaw members 102, 104 relative to one another. Thus, upper and lower jaw members 102, 104 can be locked in the open position, the closed position, and/or an intermediate position between the open and closed positions. For example, referring to FIG. 1B, upper and lower jaw members 102, 104 are biased closed and in the absence of any external force, upper and lower jaw members 102, 104 will move into the closed position. If it is desirable to maintain device 100 in the open position (FIG. 1B), a locking member can be provided. For example, such a locking member can be positioned between first arm 122 and second arm 123 (either external or internal to handle member 120) to maintain the two arms 122, 123 a desired distance apart.

Similarly, if desired, a locking mechanism can be provided to secure upper and lower jaw members 102, 104 in a closed position. Locking upper and lower jaw members 102, 104 in a closed position can be particularly desirable if the jaw members are not biased towards one another, or if upper and lower jaw members 102, 104 are biased towards the open position.

Figure 3D:
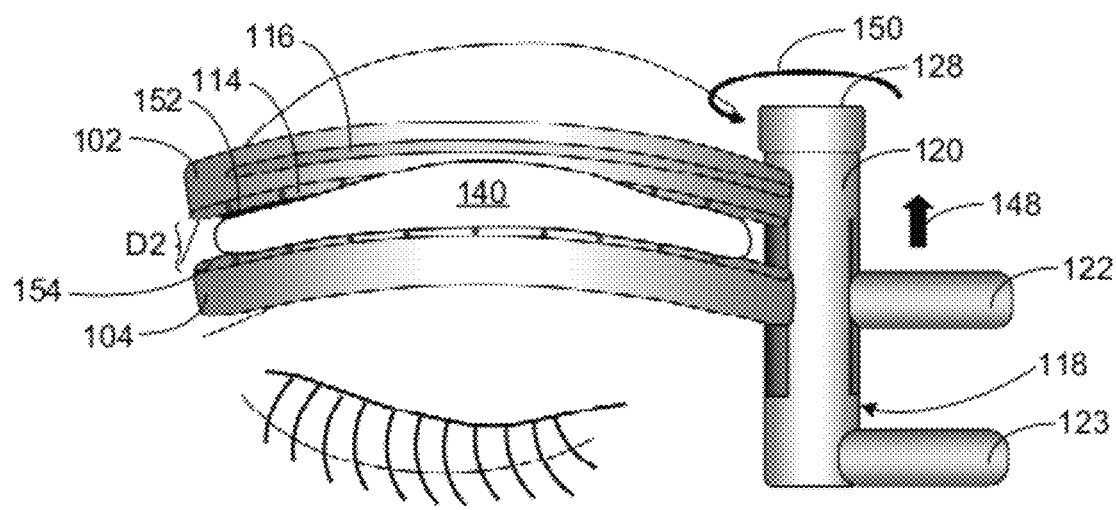
FIG. 3D illustrates the device of FIG. 3B, with the device shown in an closed position with tissue captured between clamping surfaces of the device.

FIGS. 3A-3E illustrate a method of capturing and holding eyelid tissue using device 100. Referring to FIG. 3A, an area 140 of eyelid tissue that is to be removed can first be identified. The identification of area 140 can include creating an outline 142 of area 140 using a marker or other such tool. The outline 142 can be drawn to follow the natural creases of the eye to reduce the conspicuousness of the resulting incision lines as much as possible.

FIG. 3B illustrates the application of a downward force (illustrated by arrow 144) to move upper and lower jaw members 102, 104 into the open position. As shown in FIG. 3C, device 100 can be maintained in the open position and the area 140 of eyelid tissue can be moved into position between first and second tissue contacting surfaces 106, 108. To maintain device 100 in the open position, a continuous force can be applied to first arm 122 to hold device 100 in the open position. Alternatively, a locking member (not shown) can be moved into a locked position to hold device 100 in the open position.

While device 100 is in the open position, at least a portion of area 140 can be positioned between first and second tissue contacting surfaces 106, 108. A gripping device can be used to facilitate the movement of the area 140 into the space between first and second tissue contacting surfaces 106, 108. For example, as shown in FIG. 3C, a pair of forceps 146 can grip a portion of area 140 and pull it away from the patient and into the space between first and second tissue contacting surfaces 106, 108.

To capture the area 140 between first and second tissue contacting surfaces 106, 108, device 100 can be moved into the closed position by releasing the force exerted downwardly on first arm 122 in the direction of arrow 144 (FIG. 3B). As shown in FIG. 3D, upon release of the downward force 144, first arm 122 will move in the direction of arrow 148 due to the biasing force exerted on first arm 122 by spring member 126. As first arm 122 moves in the direction of arrow 148, the distance between first and second tissue contacting surfaces 106, 108 is decreased. At that time, the distance between upper and lower jaw members can be further decreased by rotating the screw so that the threaded portion 130 engages with the thread-receiving portion to draw lower jaw member 104 closer to upper jaw member 102. Distance D2 can be adjusted by rotating the screw until the desired distance D2 (and resulting pressure on the captured tissue) is achieved.

If the screw is acting as a set screw as in the alternate embodiment described above, after first arm 122 contacts adjusting member 128, first arm 122 is restricted from moving further upwards. Thus, adjustment of the depth of the bottom surface of the screw can alter the distance D2 between first and second tissue contacting surfaces 106, 108.

The depth of adjusting member 128 can be initially set so that the distance D2 between first and second tissue contacting surfaces 106, 108 is large enough to allow some adjustment of the tissue positioned between first and second tissue contacting surfaces 106, 108. That is, D2 can be set so that only a partial gripping pressure is exerted on area 140 by first and second tissue contacting surfaces 106, 108 when device 100 is in the closed position.

Accordingly, adjusting member 128 operates to adjust the distance D2 between first and second tissue contacting surfaces 106, 108 (e.g., either by engaging with a thread-receiving portion of the lower jaw member 104 or restricting movement of the spring-biased first arm 122). Therefore, adjusting member 128 can also be considered to be a pressure adjustment member because by altering the distance D2, the amount of pressure exerted on the area 140 can be adjusted.

Figure 3E:
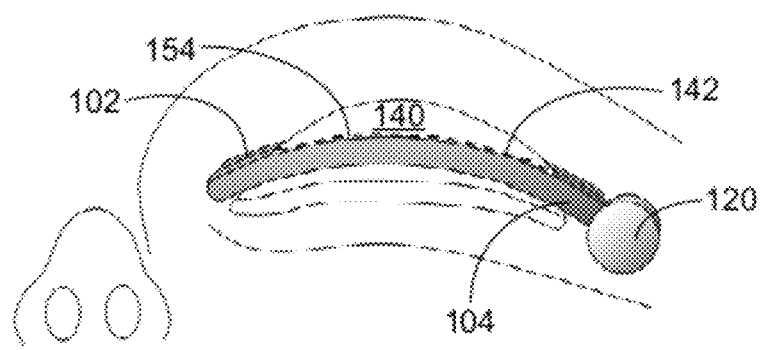
FIG. 3E illustrates a bottom view of the device of FIG. 3B, with the device shown in an closed position with tissue captured between clamping surfaces of the device.

Distance D2 can be set so that when device 100 is in the closed position, the surgeon can perform minor adjustments to the area 140 captured between the first and second tissue contacting surfaces 106, 108. Once the area 140 is manipulated into the desired position between first and second tissue contacting surfaces 106, 108, adjusting member 128 can then be rotated in the direction of arrow 150 to decrease the distance D2 between first and second tissue contacting surfaces 106, 108. The decrease in distance D2 increases the gripping force exerted on area 140 by first and second tissue contacting surfaces 106, 108. As shown in FIG. 3E, which illustrates a bottom view of device 100 coupled to the eyelid tissue of a patient, when area 140 is fully secured between first and second tissue contacting surfaces 106, 108, the outline 142 of the area 140 is preferably substantially aligned with front edges 152, 154 of the upper and lower jaw members 102, 104, respectively. If desired, additional alterations can be performed to the position of the area 140 by increasing distance D2 again to permit manipulation of the area 140 relative to first and second tissue contacting surfaces 106, 108.

After the area 140 is fully secured between first and second tissue contacting surfaces 106, 108, a cutting tool can be used to excise the tissue that extends beyond front edges 152, 154 of upper and lower jaw members 102, 104. Desirably, the tissue that extends beyond front edges 152, 154 of upper and lower jaw members 102, 104 substantially corresponds to the area 140 identified within outline 142. To excise the tissue that extends beyond front edges 152, 154, a cutting tool can be directed across front edges 152, 154. Desirably, the cutting tool has a blade or cutting area that extends across both front edges 152, 154 so that the excision of tissue can be performed in a single cutting action across front edges 152, 154. Because upper and lower jaw members 102, 104 extend from handle member 120 in a cantilevered manner, access to the desired cutting area (e.g., front edges 152, 154) can be relatively unimpeded.

Figure 4:
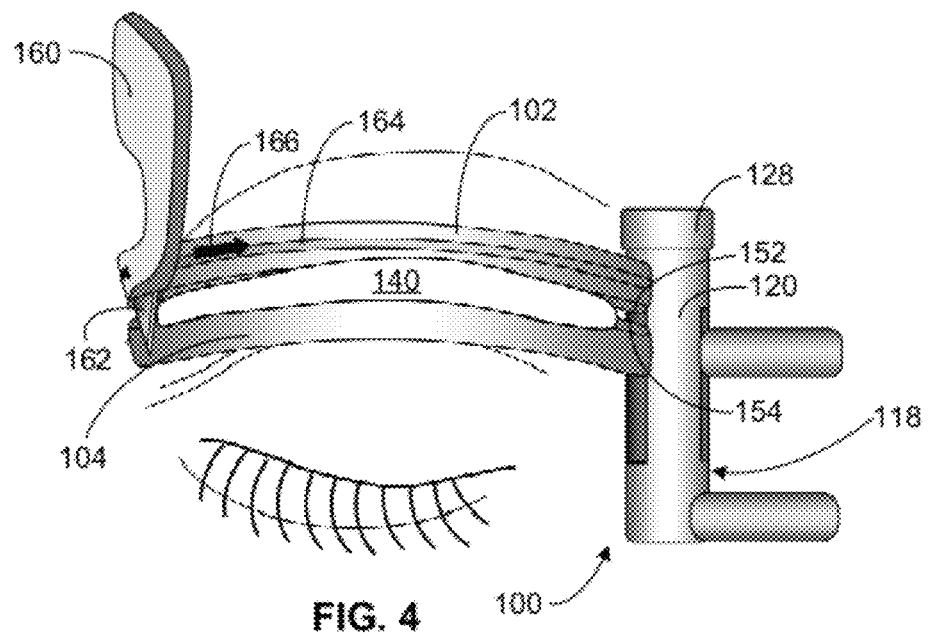
FIG. 4 illustrates a blepharoplasty device that includes a cutting tool.

Referring to FIG. 4, a cutting member 160 is illustrated. Cutting member 160 can have a cutting portion 162 (e.g., a blade) that extends across front edges 152, 154 to excise the area 140 of tissue captured between upper and lower jaw members 102, 104. To facilitate the excision of tissue and improve the consistency of the cutting process, cutting member 160 can be at least partially integrated with device 100. In one embodiment, cutting member 160 can comprise a groove that can receive a protrusion or extension 164 (e.g., a rail) that extends along the length of one or both of upper and lower jaw members 102, 104.

For example, as shown in FIG. 4, a groove on a back surface of cutting member 160 can receive rail 164, which extends along the length of upper jaw member 102. To excise the captured tissue (e.g., area 140), the rail 164 can be inserted into the groove of the cutting member 160 and cutting portion 162 can be directed across the length of the upper and lower jaw members 102, 104 in the direction indicated by arrow 166. As cutting member 160 moves across the length of upper and lower jaw members 102, 104, a back side of cutting portion 162 moves along front edges 152, 154 while cutting portion 162 cuts through the portion of the tissue that extends beyond front edges 152, 154. The back side of cutting portion 162 can contact the front edges 152, 154 to further guide the movement of cutting portion 162 and improve the accuracy of the location of the cut. In this manner, the cut performed by the cutting member 160 can be defined by the shape and profile of the front edges 152, 154 of upper and lower jaw members 102, 104. Cutting member 160 can also accurately follow the shape and profile of front edges 152, 154 as a result of the guidance offered by guide 164 and/or front edges 152, 154. Referring again to FIG. 2, the height H of the front edges 152, 154 determines the height of the cut relative to the surfaces of the upper and lower jaw members 102, 104 that face the patient.

The cutting members used herein can include various types of cutting tools. For example, the cutting members can comprise one or more sharp blades, radiofrequency cutters, microwave elements, ultrasonic cutting tips, lasers, high-pressure gas/fluid streams, or other tissue cutting means. As described above and as shown in FIG. 4, the cutting member can be configured to excise tissue by moving the cutting member across the length of upper and lower jaw members 102, 104. Alternatively, as described in more detail below, the excision of tissue by the cutting member can be performed across the width of upper and lower jaw members 102.

Figure 5:
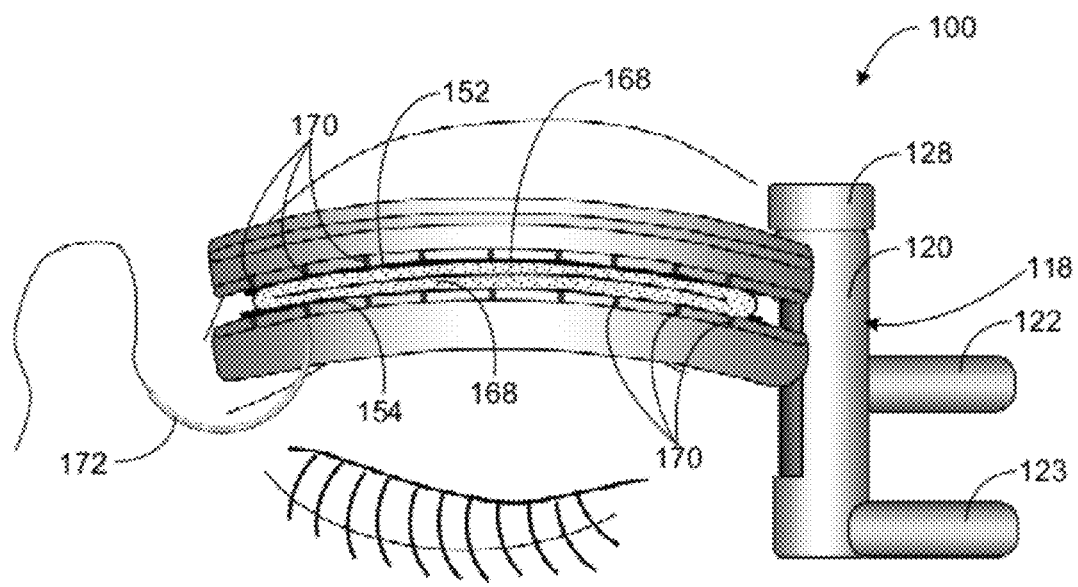
FIG. 5 illustrates a blepharoplasty device that includes a plurality of suture guides.

After the desired tissue is excised by the cutting member, the resulting edges of cut tissue 168 can be closed by sewing, stapling, and/or any other appropriate closure methods. As shown in FIG. 5, a plurality of suture guides 170 can be provided along the length of upper and lower jaw members 102, 104 to facilitate reattachment of cut tissue 168. Suture guides 170 can be spaced apart a set distance along the length of each of the upper and lower jaw members 102, 104 to allow the delivery of a suture needle 172 through the suture guides to form one or more suture loops through the edges of cut tissue 168. Front edges 152, 154 can be raised relative to other portions of upper and lower jaw members 102, 104. Suture guides 170 can be provided on the raised edges 152, 154 to improve the accessibility of suture guides 170 to the surgeon. By closing the opening in the tissue while the open tissue remains secured between first and second tissue contacting surfaces 106, 108, adjacent tissue edges can be sewn together in a precise and accurate manner with the opposing edges of cut tissue 168 being substantially aligned relative to one another.

Figure 6:
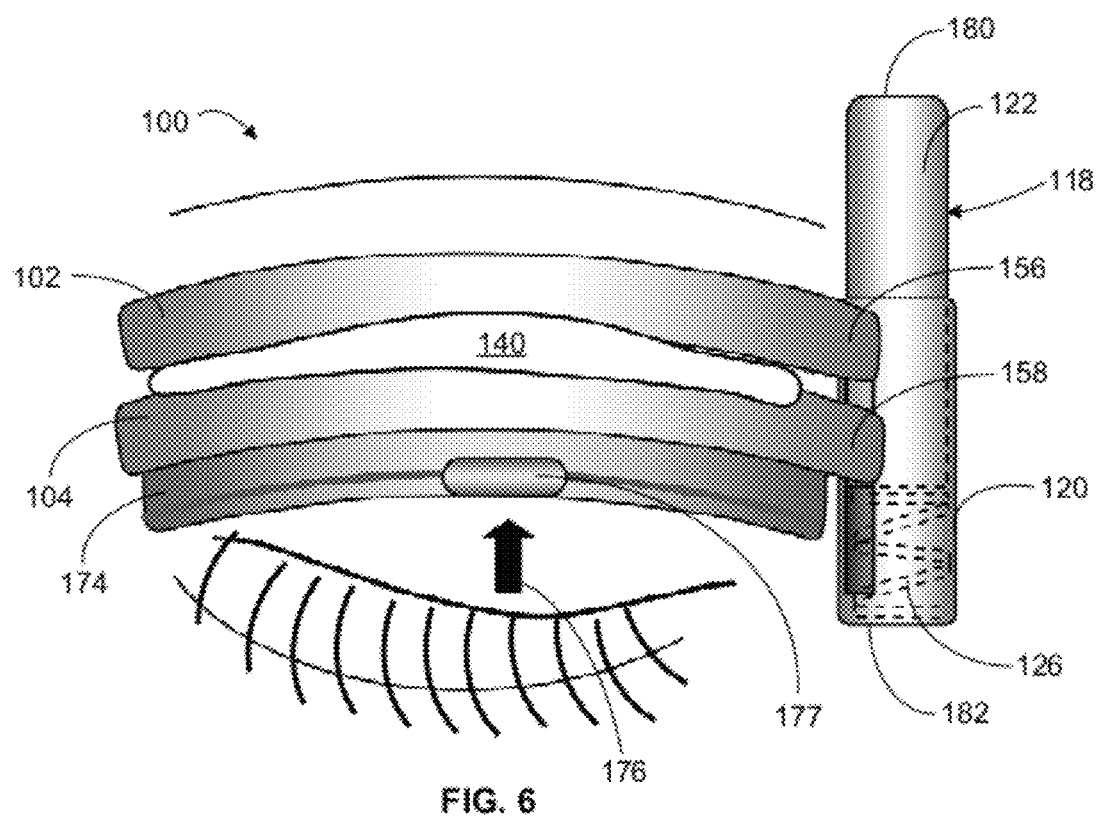
FIG. 6 illustrates a blepharoplasty device that includes a cutting tool that is vertically movable.
Figure 7:
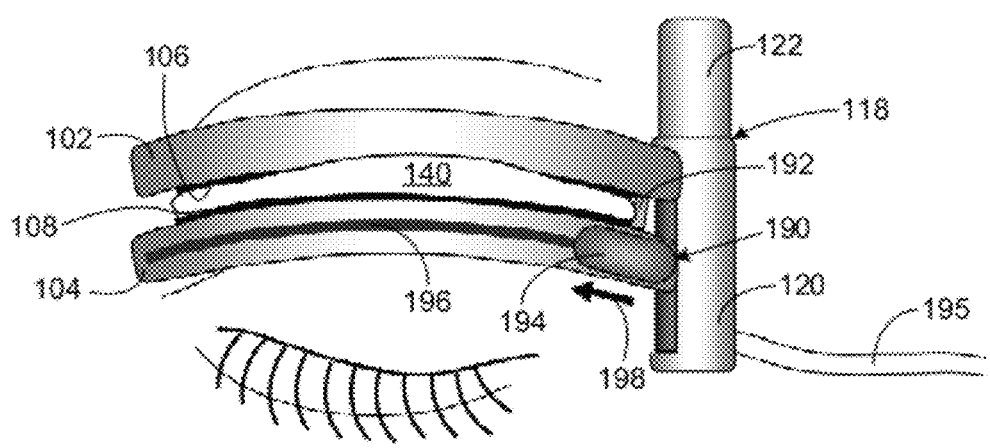
FIG. 7 illustrates a blepharoplasty device that includes a cutting tool.

FIGS. 6 and 7 illustrate other cutting mechanisms that can be integrated in the device to provide consistent and uniform cuts in tissue captured between the upper and lower jaw members 102, 104. Referring to FIG. 6, a cutting tool 174 that can provide a vertical cut to excise tissue is illustrated. Cutting tool 174 can comprise a blade that extends substantially along the length of upper and lower jaw members 102, 104. The blade can be directed through or along lower jaw member 104 and can be configured to move upward in the direction indicated by arrow 176. As the blade moves upward, tissue captured between upper and lower jaw members 102, 104 will be removed. To facilitate manual movement of the blade in the upward direction, a ledge or other gripping surface 177 can be provided. To the extent that the blade extends through lower jaw member 104, the tissue will be cut at an area just behind a plane formed by front surfaces 156, 158. Accordingly, in this embodiment, rather than aligning the outline 142 with the front edges 152, 154 (or front surfaces 156, 158), it may be desirable to position the outline 142 within an area between upper and lower jaw members 102, 104 (e.g., behind the plane formed by front surfaces 156, 158). Alternatively, the blade can extend along front surfaces 156, 158, rather than through lower jaw member 104, to provide a cut that will remove tissue that extends beyond front surfaces 156, 158 in a manner similar to other embodiments disclosed herein.

The actuator illustrated FIG. 6 differs somewhat from the structures illustrated in previous embodiments. Like the other devices, the device shown in FIG. 6 is biased towards the closed position. However, instead of extending outward from handle member 120, first arm 122 extends upwards and is generally coaxial with handle member 120. Because first arm 122 is generally coaxially aligned with handle member 120, a second arm member may not be required; instead, pressure can be exerted on first arm 122 by applying manual pressure to a top surface 180 of first arm 122 while holding handle member 120 at its bottom surface 182.

FIG. 7 illustrates a cutting tool 190 that is integrated with device 100 to facilitate the excision of tissue. Cutting tool 190 comprises a cutting portion 192 that is configured to cut an area 140 of tissue that is captured between upper and lower jaw members 102, 104. Cutting portion 192 can be movable along the length of upper and lower jaw members 102, 104. For example, a knob 194 can be coupled to cutting portion 192 to facilitate sliding cutting portion along a cutting guide 196 in the direction of arrow 198. As in previous embodiments, cutting portion 192 can cut the tissue as cutting portion 192 moves along the portion of the tissue that is captured and held between upper and lower jaw members 102, 104.

Figure 8:
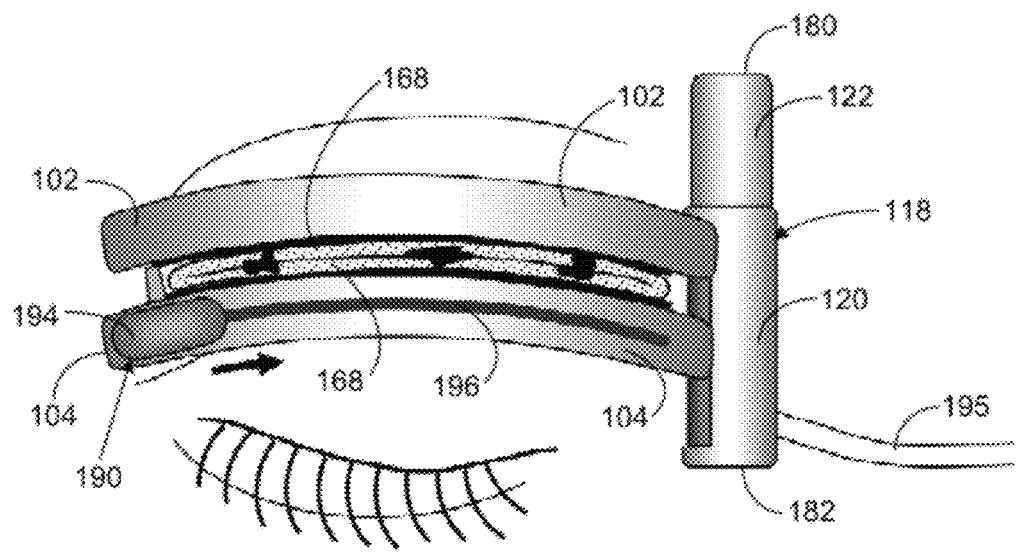
FIG. 8 illustrates the blepharoplasty device of FIG. 7, with the cutting tool also including a cauterizing tool.

FIG. 8 illustrates another embodiment of the device shown in FIG. 7. In this embodiment, cutting tool 190 also comprises a cauterizing element that can cauterize cut tissue 168 to reduce bleeding and promote healing of the cut tissue 168. The cauterizing element of cutting tool 190 can be configured to cauterize the cut tissue during the cutting process and/or after the cutting process has been performed. To provide the ability to both cut and cauterize, cutting tool 190 can comprise an element that utilizes one or more of resistance heating, high frequency electric current, microwave energy, ultrasound, laser, or other heat-generating means to promote blood coagulation.

For example, in one embodiment, the cutting portion 192 can be a radiofrequency electrode that is capable of performing both a cutting step (FIG. 7) and a cauterizing step (FIG. 8). Referring to FIG. 7, electrode cutting portion 192 can be advanced across the tissue held in position by upper and lower jaw members 102, 104. A cutting frequency can be applied to the blade to dissect the tissue as electrode cutting portion 192 is advanced across the tissue in the direction shown by the arrow 198. Next, as shown in FIG. 8, cutting portion 192 can pass across cut tissue 168 moving in the opposite direction (i.e., the direction shown by arrow 198). This time, as cutting portion 192 passes over the edges of cut tissue 168, a cauterizing frequency can be applied to induce hemostasis. If desired, an external power source can be coupled to device 100 via a cable 195 to provide power to the cutting portion 192 during the cutting step and/or the cauterizing step.

Figure 9:
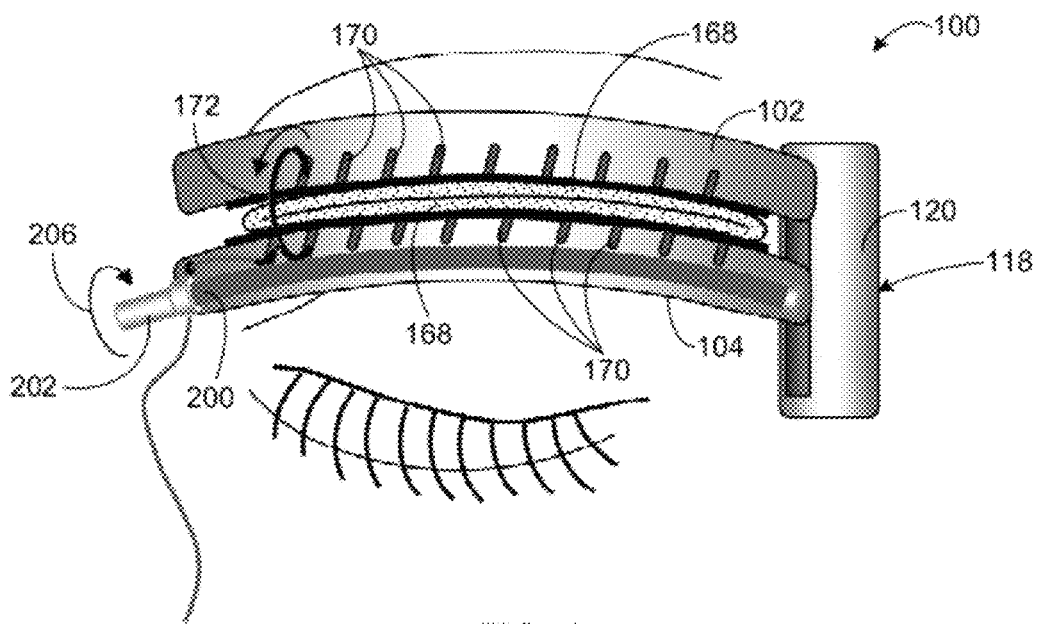
FIG. 9 illustrates a blepharoplasty device that includes a plurality of suture guides.
Figure 10:
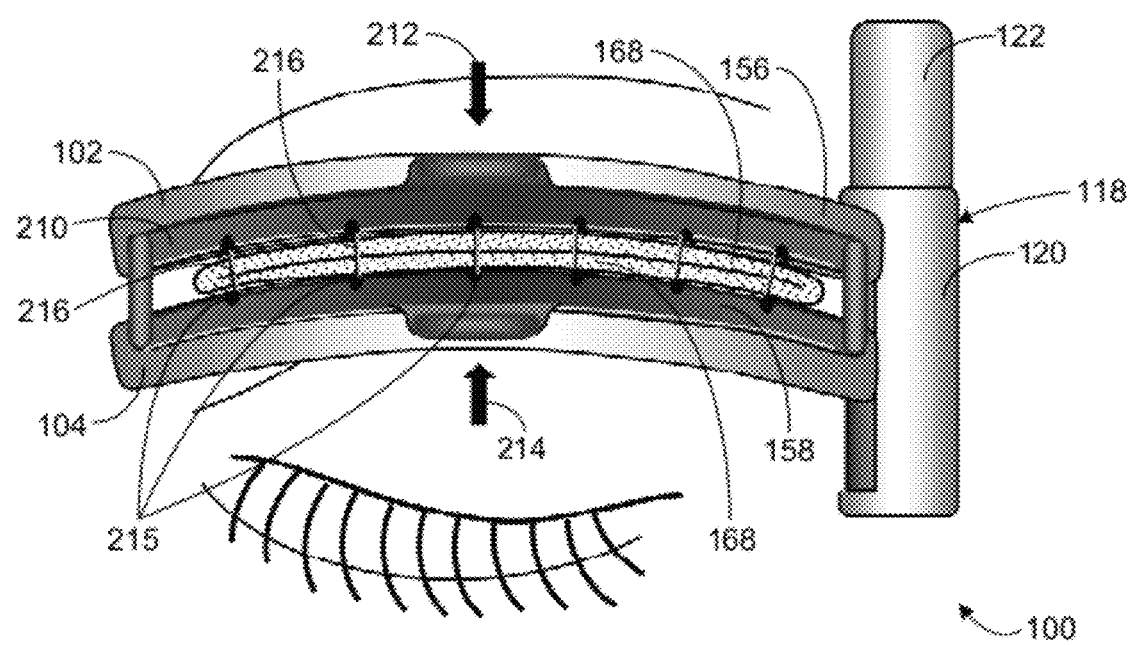
FIG. 10 illustrates a blepharoplasty device that includes a stapling mechanism.

FIGS. 9 and 10 illustrate additional embodiments for reattaching the edges of cut tissue to one another after a portion of the eyelid tissue has been excised. FIG. 9 illustrates a device 100 that includes a plurality of suture guides 170 on both upper and lower jaw members 102, 104. In addition, the device shown in FIG. 9 also includes a continuous suturing mechanism 200. Continuous suturing mechanism 200 can provide a rotatable handle portion 202 and a suture feed opening 204. By passing a suture needle 172 through the suture feed opening 204 and rotating handle portion 202 in the direction illustrated by arrow 206, the suture needle 172 (and suture coupled to the suture needle) can be continuously delivered from a suture guide 170 on one of the jaw members to another suture guide on the other jaw member. Thus, as shown in FIG. 9, suture needle 172 can be continuously delivered from one suture guide to another suture guide as indicated by arrow 208 to attach the edges of cut tissue 168 together.

FIG. 10 illustrates an embodiment in which device 100 includes a staple attachment device 210 for placing multiple staples across cut tissue 168. As shown in FIG. 10, staple attachment device 210 can be positioned along front surfaces 156, 158 of upper and lower jaw members 102, 104. By applying a downward force (arrow 212) on a top portion of staple attachment device 210 and an upward force (arrow 214) on a bottom portion of staple attachment device 210, a plurality of staples 216 can be delivered at the edges of cut tissue 168 to close the incision. The staple attachment device 210 can provide a plurality of guide slots 215 for receiving a stapling instrument or for allowing use of a stapling attachment that can deliver multiple staples 216 in a single step. In other embodiments, the devices disclosed herein can be configured so that a layer of bonding agent can be easily applied to the edges of cut tissue as the edges are held together by upper and lower jaw members 102, 104.

Figure 11A:
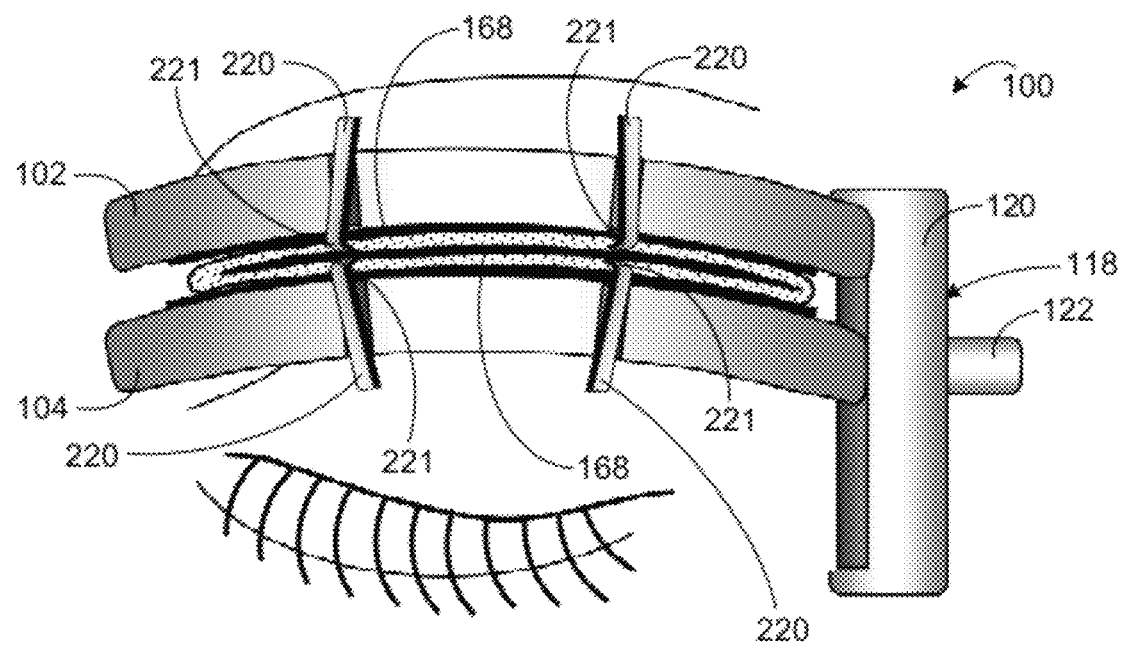
FIG. 11 illustrates a blepharoplasty device that includes a plurality of retraction members.
Figure 11B:
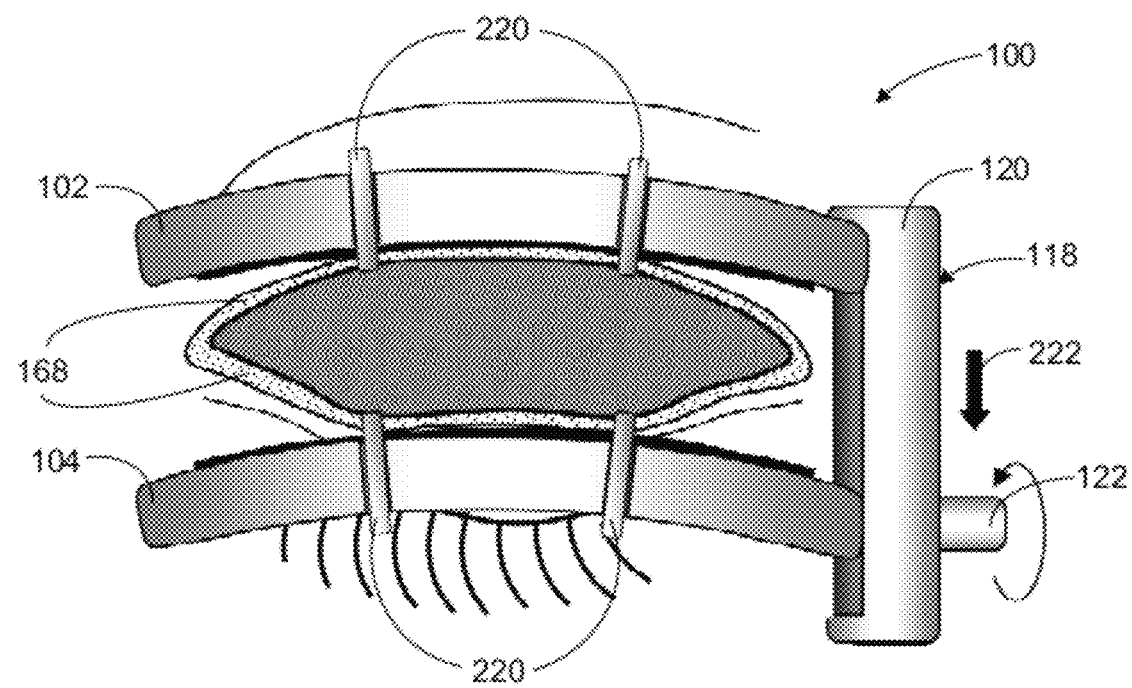
Figure 11C:
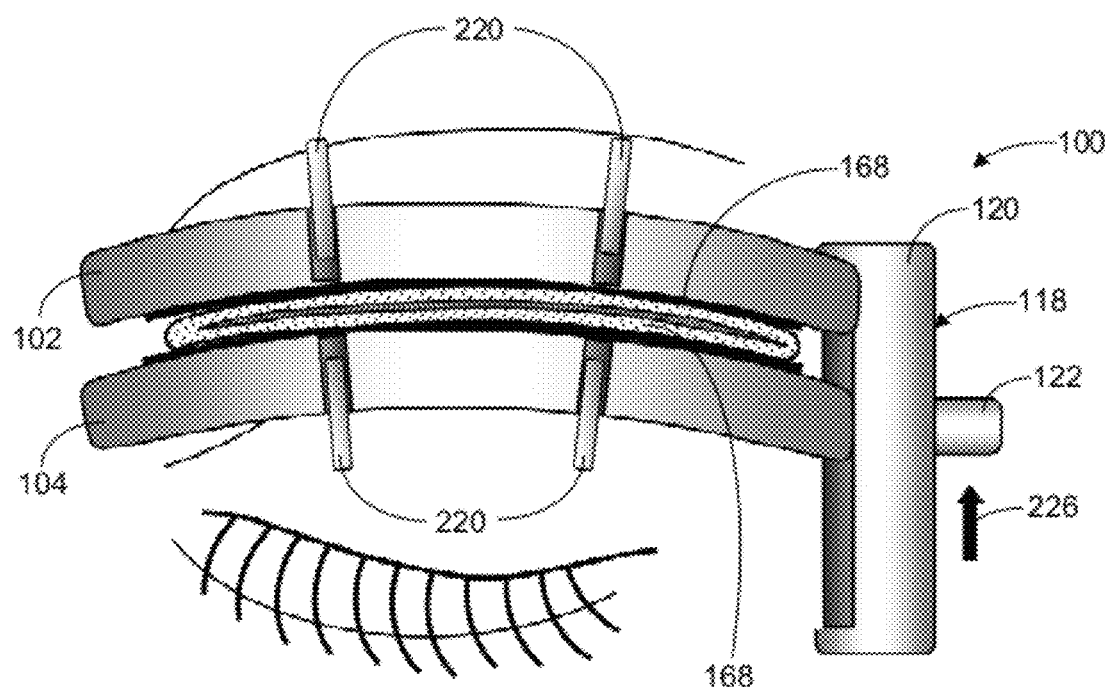

FIGS. 11A-11C illustrate an embodiment in which device 100 includes a plurality of retraction hooks 220 configured to retract tissue 168 after it has been cut by a cutting step as described in the various embodiments herein. Tissue retractors 220 can comprise hooks 221 or other curved members connected to the interior edges of upper and lower jaw members 102, 104. Tissue retractors 220 can be built into the device 100 to allow upper and lower jaws 102, 104 to capture the edges of cut tissue 168 and pull them apart from one another when device 100 is moved into the open position (FIG. 11B). Device 100 can be moved into the open position by applying a downward force 222 to first arm 122. By retracting the edges of cut tissue 168 in this manner, the surgeon can hold the eyelid incision open to facilitate the removal of fat pockets or other materials from beneath the orbital septum. As shown in FIG. 11C, once the additional tissue is removed from within the incision, device 100 can be moved back into the closed position to bring the edges of cut tissue 168 back together for suturing and hooks 221 can be removed from contact with cut tissue 168. Thus, the downward force 222 can be released to allow a biasing force 226 to move lower jaw member 104 back towards upper jaw member 102 and into the closed position. As shown in other embodiments, upper and lower jaw members can also be equipped with suture guides or other elements to help facilitate the attachment of the edges of cut tissue 168.

Various Methods and Systems for Non-Surgical Removal of Excess Skin/Tissue

In some cases, it is desirable to remove or reduce excess tissue without surgery (i.e., without physically cutting portions of the tissue with a scalpel or other cutting tool. For example, some individuals are reluctant to submit to surgical procedures. In addition, for patients whose condition cannot be documented as medically-necessary, the surgery may not covered by insurance and the cost of a surgical procedure can be a deterrent. Moreover, in many parts of the world, people who would benefit from the procedure cannot access it since surgery can be relatively expensive—even minor surgery.

Accordingly, the following embodiments provide a non-surgical option for achieving upper eyelid lifting and tightening. Such embodiments comprise methods and systems for implementing a non-surgical, patient-directed, low-cost solution for eyelid sagging that provides consistent results, positive healing, and few complications. The disclosed exemplary embodiments comprise relatively low-profile devices that can be temporarily placed on excess eyelid tissue to occlude the blood flow to skin such that the affected tissue eventually withers and sloughs off.

Figure 12:
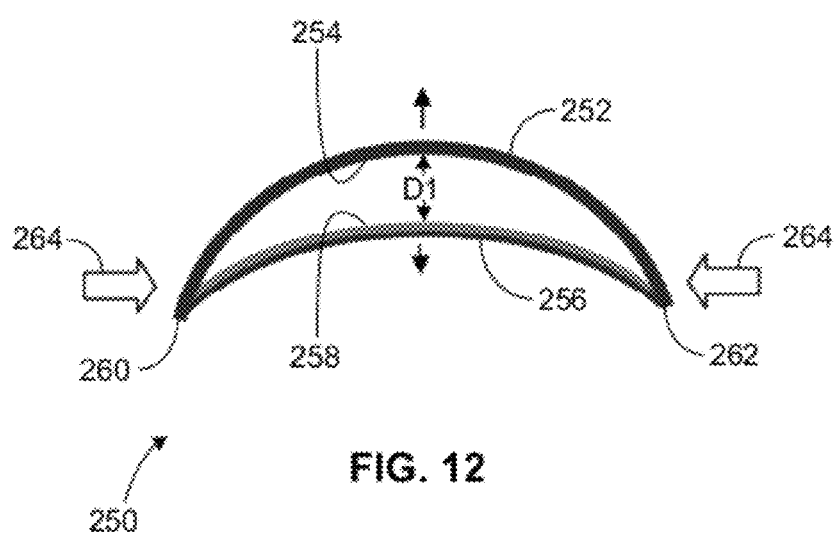
FIG. 12 illustrates a blepharoplasty device that comprises a pair of upper and lower elongate members coupled together.
Figure 13:
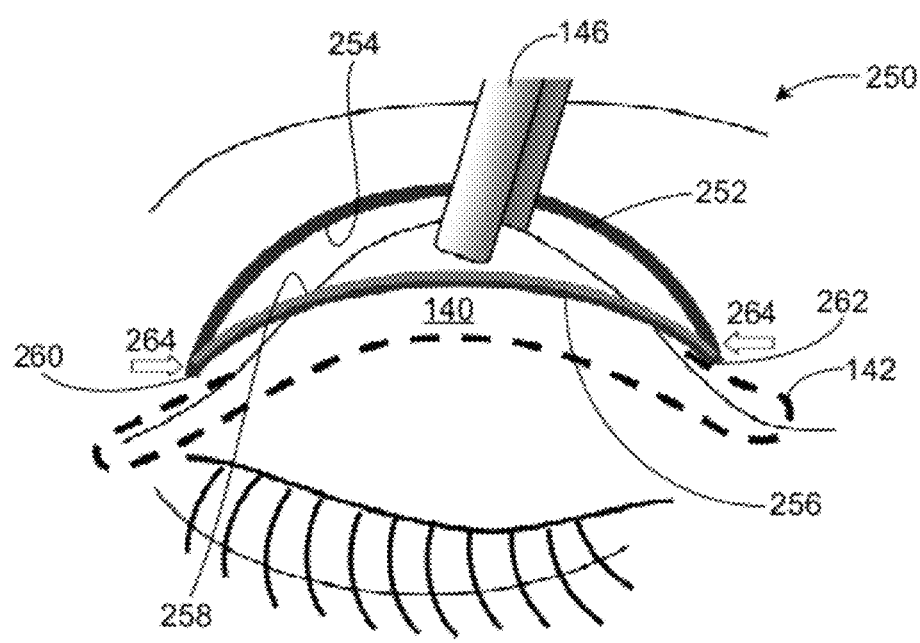
FIG. 13 illustrates the blepharoplasty device shown in FIG. 12, with the device shown in an position for receiving tissue between the pair of upper and lower elongate members.
Figure 14:
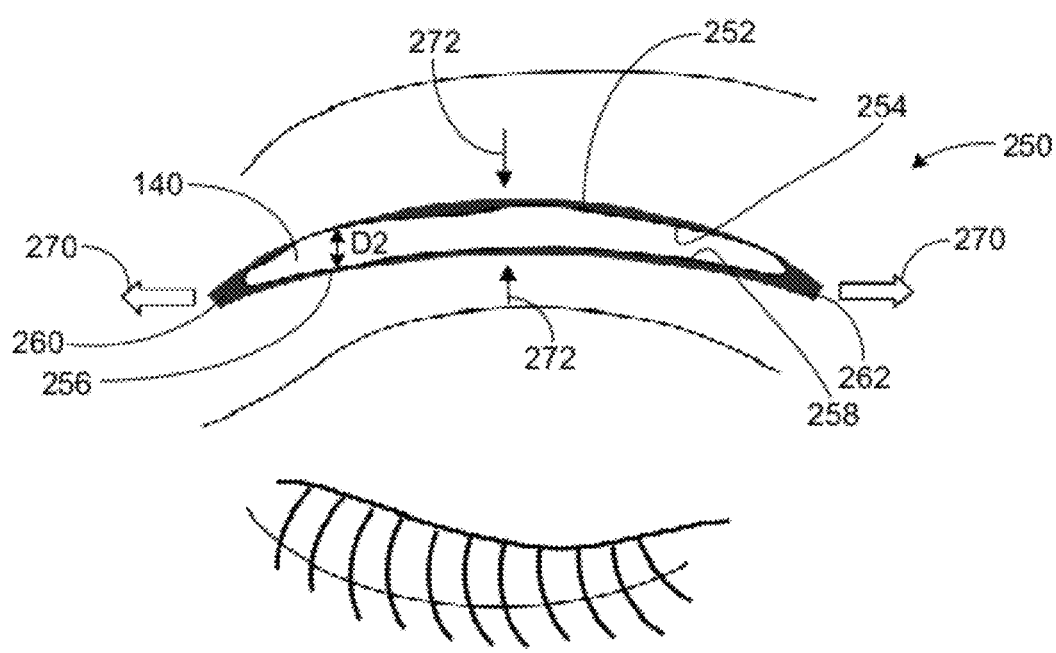
FIG. 14 illustrates the blepharoplasty device shown in FIG. 12, with the device shown in the closed position with tissue captured between the pair of upper and lower elongate members.

FIGS. 12-14 illustrate an embodiment of a non-surgical device for performing blepharoplasty. Referring to FIG. 12, device 250 can comprise another clamping element that is capable of capturing tissue between two tissue contacting surfaces. As shown in FIG. 12, device 250 comprises an upper portion 252 with a first tissue contacting surface 254 and a lower portion 256 with a second tissue contacting surface 258. Upper portion and lower portion 252, 256 can be coupled to one another at a first end 260 and a second end 262. As shown in FIG. 12, upper and lower portions 252, 256 can comprise a pair of curved elongate members.

First and second tissue contacting surfaces 254, 258 can be biased towards one another in a spring-loaded manner. To move first and second tissue contacting surfaces 254, 258 apart into the open position shown in FIG. 12, a compressive force 264 can be applied to the first and second ends 260, 262 of device 250. Alternatively, a device (e.g., a retractor or other tool) can be used to separate first and second tissue contacting surfaces 254, 258 by applying a separating force to upper and lower portions 252, 256. In the open position, first and second tissue contacting surfaces 254, 258 are separated by a distance D1. As in previous embodiments, distance D1 is large enough to allow eyelid tissue to be moved into the space between first and second tissue contacting surfaces 254, 258.

A pair of devices 250 can be fitted and applied by a physician (or other medical professional) onto a patient. The physician can determine the location and amount of excess skin to be removed and mark the area appropriately. Referring again to FIG. 3A, before using device 250, an outline 142 of an area 140 of eyelid tissue that is to be excised can be drawn on the patient. The marked area of skin can be drawn into device 250 so that device 250 applies pressure along the edges of outlined skin. As device 250 is maintained in the open position (e.g., by maintaining force 264 on ends 260, 262), at least a portion of area 140 can be positioned between first and second tissue contacting surfaces 254, 258. As in previous embodiments, a gripping device, such as forceps 146, can be used to facilitate the movement of the area 140 into a space between first and second tissue contacting surfaces 254, 258.

To capture the area 140 between first and second tissue contacting surfaces 254, 258, device 250 can be moved into the closed position by releasing the compressive force 264 exerted on ends 260, 262. As shown in FIG. 14, upon release of the compressive force 264, ends 260, 262 move away from one another in the direction of arrow 270 due to the spring-loaded nature of device 250. As ends 260, 262 move apart from one another, the distance between first and second tissue contacting surfaces 254, 258 is decreased to a distance D2. An inward force 272 is directed towards the area 140 of tissue positioned between first and second tissue contacting surfaces 254, 258. Distance D2 is configured to be sufficiently small so that the portion of area 140 received between first and second tissue contacting surfaces 254, 258 will be captured and secured therebetween.

The inward force 272 exerted by device 250 on the eyelid tissue occludes blood flow to the portion of the area 140 that is captured between first and second tissue contacting surfaces 254, 258. Desirably, the force 272 applied to the captured tissue is generally uniform along the length of the upper and lower portions 252, 256 so that the captured tissue is compressed along its length with substantially uniform and consistent pressure.

The clips can be worn by a patient for several days until the excess skin falls off or is ready for removal. In some embodiments, the clips can be worn for about 4 to 8 days to remove the excess skin and/or prepare the excess skin for removal. By maintaining sufficient pressure (inward force 272) on the eyelid tissue positioned between first and second tissue contacting surfaces 254, 258, device 250 can induce necrosis on the captured eyelid tissue while at the same time causing adherence of the edges of the tissue adjacent the tissue undergoing necrosis. After device 250 is worn a sufficient period of time, the dead tissue between first and second tissue contacting surfaces 254, 258 will slough off and the adjacent edges of the removed tissue will be adhered together. After the dead tissue sloughs off, device 250 can simply fall off the patient along with the dead tissue. Alternatively, device 250 can be removed after a sufficient amount of necrosis and closure of the remaining tissue is achieved. If necessary, any remaining excess and/or dead tissue can be excised.

Therefore, device 250 causes the tissue between first and second tissue contacting surfaces 254, 258 to be removed without requiring any incisions in the eyelid tissue, and device 250 causes the edges of adjacent tissue to be closed without requiring any active suturing or other closure steps by the surgeon. However, depending on the desired results and/or the effectiveness of device 250 to remove and close tissue, it may be desirable to excise a small amount of tissue and/or to further seal the tissue together (e.g., by suturing or other means).

Upper and lower portions 252, 256 can be coupled together in a biased manner using a various mechanisms. For example, device 250 can be formed by an integrated spring mechanism as described above with respect to FIGS. 12-14. Alternatively, other mechanisms can be provided to couple upper and lower portions 252, 256 together in an inwardly biased manner, including, for example, the use of cable-based tensioning devices and/or forming one or more portions of device 250 from shape member materials.

FIGS. 15A and 15B illustrate another embodiment of a non-surgical device for performing blepharoplasty. Device 280 comprises an upper portion 252 with a first tissue contacting surface 254 and a lower portion 256 with a second tissue contacting surface 258. Upper portion and lower portion 252, 256 can be coupled to one another at a first end 260 and a second end 262. FIG. 15A illustrates device 280 in a biased closed position and FIG. 15B illustrates device 280 in an open position.

As shown in FIGS. 15A and 15B, first and second ends 260, 262 can comprise a spring member, such as a rounded spring member biased towards the closed position (FIG. 15A). As shown in FIG. 15B, to separate first tissue contacting surface 254 and second tissue contacting surface 258, a separating force 282 can be applied to device 280. Force 282 can be applied by any conventional device capable of separating upper and lower portions 252, 256. As shown and described with respect to FIGS. 12-14, an area of tissue can be moved between first tissue contacting surface 254 and second tissue contacting surface 258, and force 282 can be removed and/or reduced to allow first tissue contacting surface 254 and second tissue contacting surface 258 to move closer together (e.g., from a distance D1 to a distance D2) to secure the area of tissue therebetween.

FIGS. 16A and 16B illustrate another embodiment of a non-surgical device for performing blepharoplasty. Device 290 is similar to device 280 (FIGS. 15A and 15B), except that first and second ends 260, 262 comprise stretchable members that couple upper portion 252 and lower portion 256 together. The stretchable members can be made of various materials, so long as they are capable of biasing device 290 towards the closed position (FIG. 16A). Stretchable members can be stretched to permit first tissue contacting surface 254 and second tissue contacting surface 258 to be separated a sufficient distance (e.g., distance D1) to allow an area of tissue to be moved between the first tissue contacting surface 254 and second tissue contacting surface 258 when they are moved into the open configuration (FIG. 16B). In some embodiments, the stretchable member can comprise a silicone material that secures upper and lower portions 252n 256 to one another.

FIG. 17 illustrates another embodiment of a non-surgical device for performing blepharoplasty. Device 300 is generally similar to device 250 (FIG. 12), except that upper and lower portions 252, 256 comprise a pair of generally flat surfaces instead of the more narrow (e.g., rounded) surfaces shown in FIG. 12.

Figure 18A:
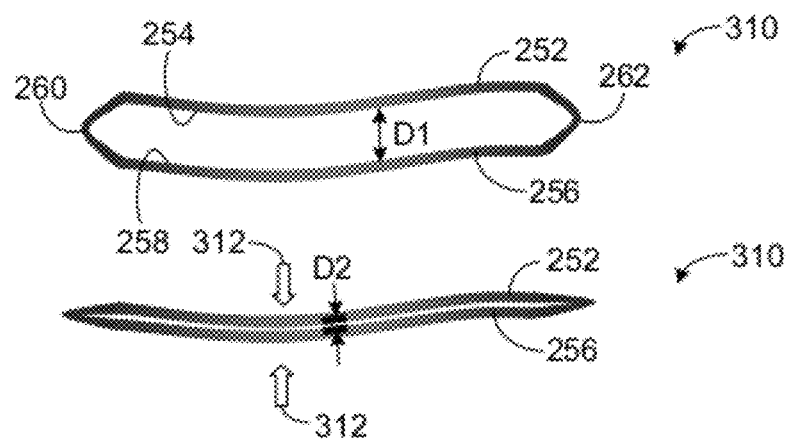
FIG. 18A illustrates another blepharoplasty device that comprises a pair of upper and lower elongate members coupled together, shown in an open position.
Figure 18B:
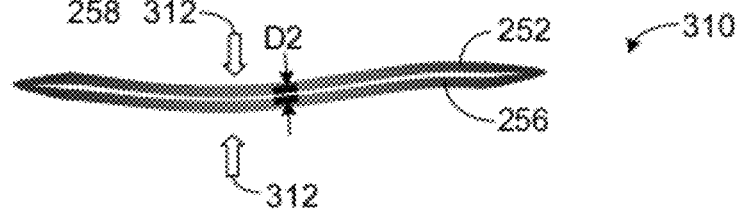
FIG. 18B illustrates the blepharoplasty device of FIG. 18A, shown in a closed position.

FIGS. 18A and 18B illustrate another embodiment of a non-surgical device for performing blepharoplasty. Device 310 is configured so that it is initially in an open configuration as shown in FIG. 18A. The exertion of a compressive force, as indicated by arrows 312, causes first tissue contacting surface 254 and second tissue contacting surface 258 to move from a first distance apart D1 (FIG. 18A) to a second distance apart D2 (FIG. 18B). Thus, device 310 is a device that can be maintained in an open position (FIG. 18A) until a sufficient amount of compressive force is applied, causing device to move into a closed position (FIG. 18B).

In some embodiments, ends 260, 262 can comprise temporary locking means that maintain device 310 in the open position. Compressive force 312 overcomes the temporary locking means and causes the temporary locking means to collapse, weaken, and/or otherwise cease restricting the inward movement of first tissue contacting surface 254 and second tissue contacting surface 258 relative to one another.

Figure 19A:
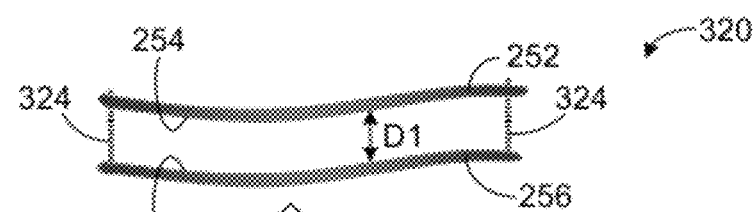
FIG. 19A illustrates another blepharoplasty device that comprises a pair of upper and lower elongate members coupled together, shown in an open position.
Figure 19B:
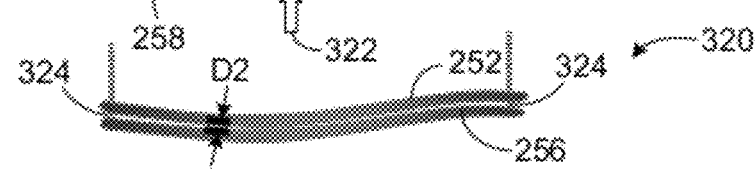
FIG. 19B illustrates the blepharoplasty device of FIG. 18A, shown in a closed position.
Figure 19C:
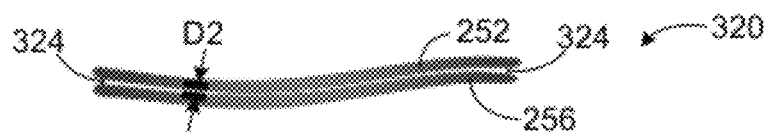
FIG. 19C illustrates the blepharoplasty device of FIG. 18A, shown in a closed position.

FIGS. 19A-19C illustrate another embodiment of a non-surgical device for performing blepharoplasty. Device 320 is configured so that it is initially in an open configuration as shown in FIG. 19A. A pair of locking members or fasteners 324 couple upper and lower portions 252, 256 together. The locking members can comprise one-way locking members, such as a locking member that has teeth that are configured allow upper and lower portions 252, 256 to be moved closer together, while restricting movement of upper and lower portions 252, 256 in a direction that increases the distance between upper and lower portions 252, 256. Such locking members can comprise a serrated pin that functions similar to a cable tie to allow upper and lower portions 252, 256 to move together into a closed position (FIG. 19B). Once upper and lower portions 252, 256 are locked into the closed position (FIG. 19B), excess portions of locking members 324 (e.g., those portions that extend beyond the upper and lower portions 252, 256) can be removed, such as by cutting or trimming off the excess portions. FIG. 19C shows upper and lower portions 252, 256 locked together by locking members 324 that have had excess portions removed.

Figure 20A:
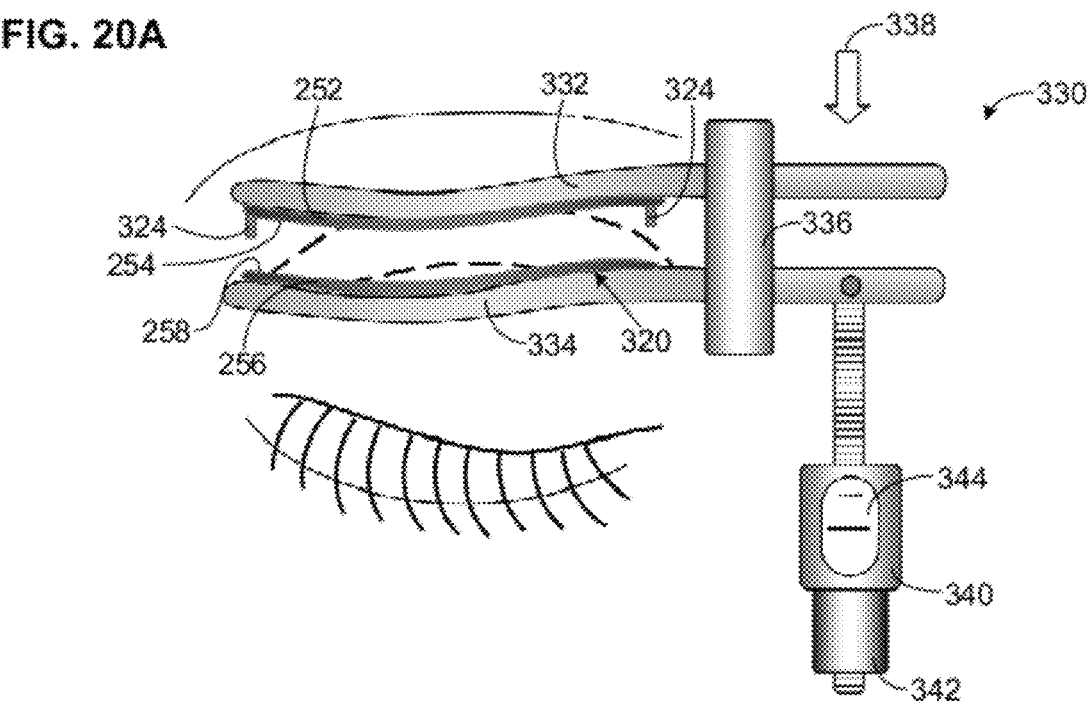
FIG. 20A-20D illustrate tools for applying a blepharoplasty device to a patient.

FIGS. 20A-20D illustrate a tool 330 that can be used in combination with device 320 to move upper and lower portions 252, 256 towards one another into a locked position. Tool 330 can comprise a pair of upper and lower arms 332, 334 coupled by at least one linking member 336. As shown in FIG. 20A, upper and lower arms 332, 334 can be positioned adjacent upper and lower portions 252, 256 of a non-surgical device (such as device 320) when the device is in an open position (or an intermediate position between the open and closed positions). A force 338 (e.g., a manually-applied force) can be applied to one or both of upper and lower arms 332, 334 to move the arms closer together. As the arms 332, 334 move closer together, inner surfaces of the arms 332, 334 contact upper and lower portions 252, 256, moving those elements closer together.

Figure 20B:
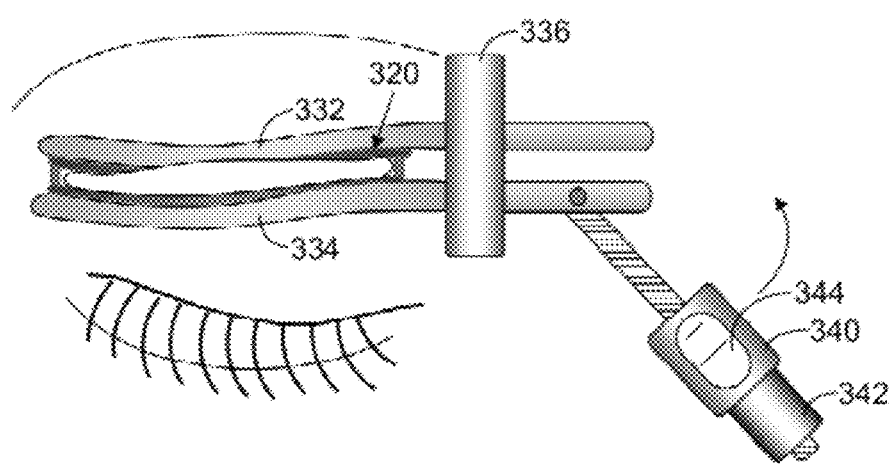
Figure 20C:
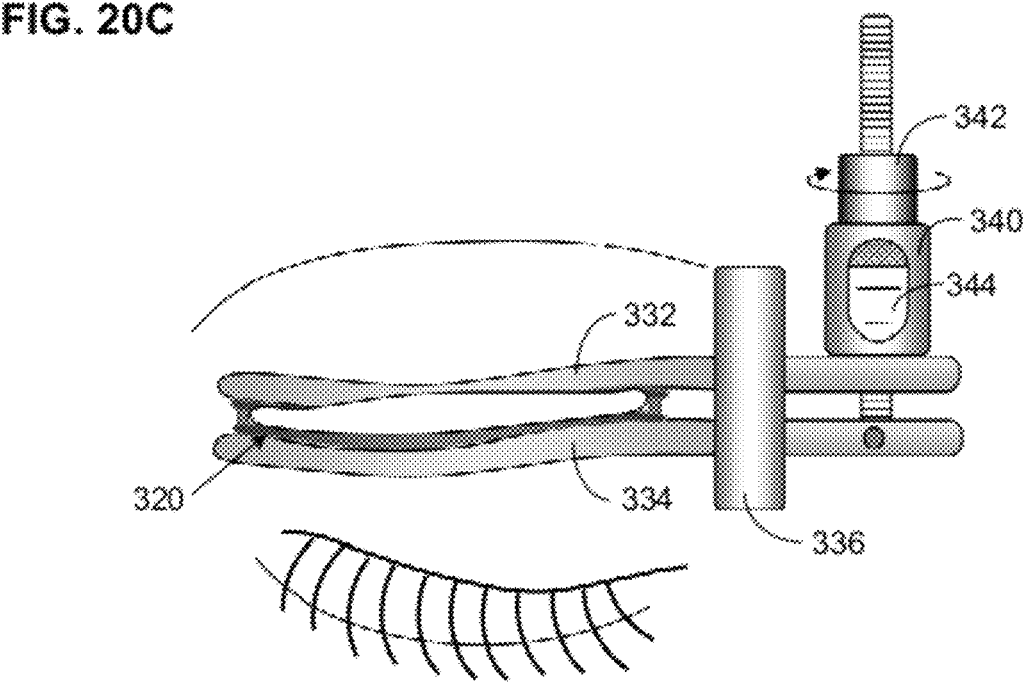
Figure 20D:
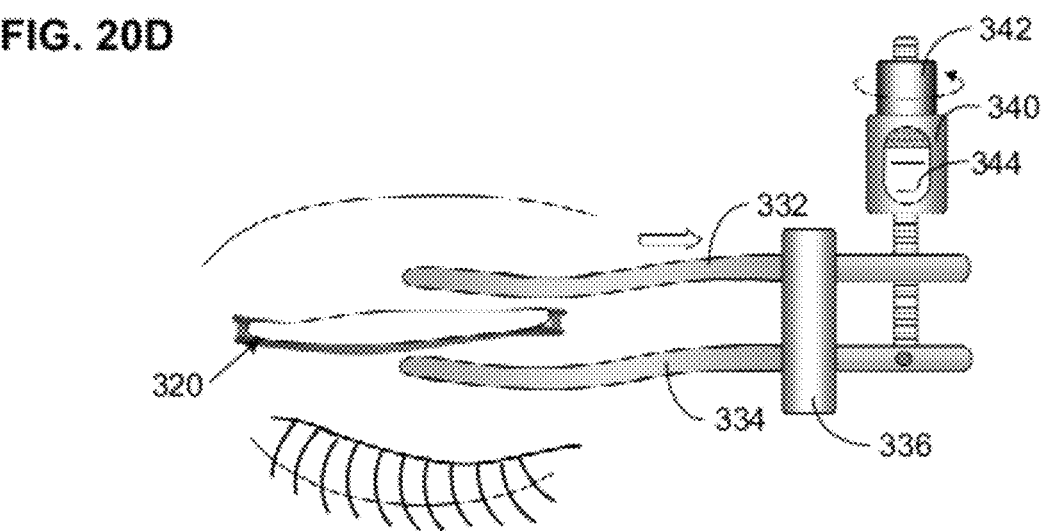

As shown in FIG. 20B, once upper and lower portions 252, 256 move into a partially closed position, an additional force can be applied to the arms 332, 334 by a force applicator 340. Applicator 340 can be rotated, if necessary, as shown in FIG. 20B, so that it is positioned to apply a force to arms 332, 334. For example, as shown in FIG. 20C, a compressive force can be applied to arms 332, 334 (and hence, to upper and lower portions 252, 256) by rotating a threaded member 342. Preferably, an indicator 344 is provided to indicate the amount of force applied to arms 332, 334 by applicator 340. Accordingly, applicator 340 can provide an accurate tool for applying a desired amount of pressure to upper and lower portions 252, 256 of device 320. Once the desired amount of pressure is applied, applicator 340 can be removed as shown in FIG. 20D, such as by rotating threaded member 342 in an opposite direction to cause arms 332, 334 to move apart. After arms 332, 334 are moved far enough apart, device 330 can be removed, leaving behind device 320 with a desired portion of tissue captured between first tissue contacting surface 254 and second tissue contacting surface 258.

The various devices disclosed herein can be constructed in shapes and configurations specifically shaped for use with either a left eye and/or a right eye of a patient. In addition, features of different embodiments can be combined in various ways. For example, the continuous suturing mechanism disclosed in FIG. 9 can be combined with a device that has a plurality of retractors such as that disclosed in FIG. 11A. Using the resulting device, the captured tissue can be cut, then retracted for removing fat pockets beneath the orbital septum, and then closed for delivery of sutures using the continuous suturing mechanism. This combination is provided as an example of a combination of elements from the different embodiments disclosed herein; it should be understood that any combination of the above features is contemplated, unless such combination is directly contrary to the disclosure and figures included herein as they would be understood by one of ordinary skill in the art.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A blepharoplasty device comprising:
a handle member;
an elongate, curved first jaw member coupled to the handle member and having a first tissue contacting surface;
an elongate, curved second jaw member coupled to the handle member and having a second tissue contacting surface, the first and second jaw members being moveable relative to one another between a closed position and an open position, the first and second tissue contacting surfaces being spaced apart a distance D1 in the open position and the first and second tissue contacting surfaces being spaced apart a distance D2 in the closed position;
a biasing member configured to bias the device towards the closed position; and an actuator provided on the handle member and configured to counter the biasing member and move the device into the open position; and
a cutting guide formed in one or both of the first and second jaw members and configured to receive a portion of a cutting tool to guide the tool across at least a portion of a length of the first and second jaw members,
wherein the distance D2 is smaller than the distance D1, and the distance D1 is sized to allow the insertion of eyelid tissue between the first and second tissue contacting surfaces and the distance D2 is sized to capture and secure the eyelid tissue inserted between the first and second tissue contacting surfaces.

2. The device of claim 1, wherein the first jaw member is fixedly coupled to the handle member and the second jaw member is movable relative to the handle member to allow relative movement of the first and second jaw members.

3. The device of claim 2, wherein the actuator comprises an arm member that is fixedly coupled to the second jaw member and movement of the arm member relative to the handle causes the device to move between the closed and open positions.

4. The device of claim 3, wherein the biasing member comprises a spring member that is coupled to the arm member, the spring member exerting a force on the arm member to bias the second jaw member towards the first jaw member.

5. The device of claim 3, wherein the first and second jaw members extend from the handle member in a generally cantilevered manner, and the handle member has a main body that extends generally perpendicularly to the first and second jaw members.

6. The device of claim 5, wherein the arm member extends perpendicularly from the main body of the housing member.

7. The device of claim 1, further comprising a pressure adjustment member that is moveable between a first position and a second position to adjust the distance D2, thereby varying a pressure exerted on the first and second tissue contacting surfaces in the closed position.

8. The device of claim 7, wherein the pressure adjustment member is moveable to decrease the distance D2 and increase the pressure on eyelid tissue captured between the first and second tissue contacting surfaces.

9. The device of claim 8, wherein the pressure adjustment member comprises a set screw.

10. The device of claim 1, further comprising a cutting tool that is received in the cutting guide provided in the device, the cutting tool being moveable across the at least a portion of the length of the first and second jaw members of the device to cut a portion of the eyelid tissue in a predetermined path defined by the cutting guide.

11. The device of claim 10, wherein the cutting tool comprises an electrode cutting blade that is configured to operate at a first cutting frequency and a second cauterizing frequency.

12. The device of claim 1, further comprising a cutting tool that is received in the cutting guide, the cutting tool being vertically movable between the first and second jaw members to cut a portion of the eyelid tissue in a predetermined path defined by the cutting guide.

13. The device of claim 1, further comprising a plurality of suture guides formed in the first and second jaw members.

14. The device of claim 13, further comprising a continuous suturing mechanism, the continuous suturing mechanism comprising a rotatable member configured to direct a suture needle through the plurality of suture guides.

15. The device of claim 1, further comprising a stapling device coupled to the first and second jaw members, the stapling device configured to deliver staples to attach portions of the eyelid tissue in the closed position.

16. The device of claim 1, further comprising a plurality of retraction members coupled to the first and second jaw members, the retraction members being configured to grip portions of the eyelid tissue while the device is in the closed position, wherein movement of the device to the open position causes adjacent edges of the eyelid tissue to separate.

17. The device of claim 1, wherein the first and second tissue contacting surfaces comprise cushion members that extend from inner surfaces of the first and second jaw members.

* * * * *